US007732145B2

(12) United States Patent
Kang et al.

(10) Patent No.: US 7,732,145 B2
(45) Date of Patent: Jun. 8, 2010

(54) METHOD AND DEVICES FOR RAPID DIAGNOSIS OF FOOT-AND-MOUTH DISEASE

(75) Inventors: Je-Mo Kang, Princeton, NJ (US); Nam-Kyu Shin, Incheon (KR); In-Soo Cho, Kyunggi-do (KR); Bang-Hun Hyun, Seoul (KR); Kwang-Nyeong Lee, Kyunggi-do (KR); Jae-Ku Oem, Seoul (KR); Soo-Jeong Kye, Seoul (KR); Young-Joon Ko, Kyunggi-do (KR); Bok-Kyung Ku, Kyungsangnam-do (KR); Soo-Hwan An, Seoul (KR); In-Joong Kim, Seoul (KR); Ok-Kyung Kim, Seoul (KR); Hee-Jong Kim, Kyungsangbuk-do (KR); Ki-Yong Jang, Seoul (KR); Suh-Ha Hwang, Kyunggi-do (KR); Chang-Ho Kim, Seoul (KR); Song-Woo Ko, Seoul (KR); Yi-Seok Joo, Seoul (KR)

(73) Assignees: Princeton Biomeditech Corporation, Princeton, NJ (US); Republic of Korea (National Veterinary Research & Quarantine Service), Kyonggi-Do (KR)

( * ) Notice: Subject to any disclaimer, the term of this patent is extended or adjusted under 35 U.S.C. 154(b) by 0 days.

(21) Appl. No.: 10/833,933

(22) Filed: Apr. 28, 2004

(65) Prior Publication Data
US 2006/0127885 A1 Jun. 15, 2006

(30) Foreign Application Priority Data
Apr. 28, 2003 (KR) ............... 10-2003-0026809

(51) Int. Cl.
| | |
|---|---|
| G01N 15/06 | (2006.01) |
| G01N 21/00 | (2006.01) |
| G01N 31/22 | (2006.01) |
| G01N 33/53 | (2006.01) |
| G01N 33/543 | (2006.01) |
| G01N 33/544 | (2006.01) |
| G01N 33/566 | (2006.01) |
| G01N 21/75 | (2006.01) |
| G01N 21/77 | (2006.01) |
| C12Q 1/00 | (2006.01) |
| C12M 1/34 | (2006.01) |
| C12M 3/00 | (2006.01) |

(52) U.S. Cl. ............... 435/7.1; 422/55; 422/57; 422/58; 422/61; 422/68.1; 422/82.05; 435/4; 435/287.1; 435/287.2; 435/287.7; 436/501; 436/518; 436/528; 436/166; 436/169; 436/811

(58) Field of Classification Search ............... 422/55, 422/57, 58, 61, 68.1, 82.05; 435/4, 7.1, 287.1, 435/287.2, 287.7; 436/501, 518, 528, 166, 436/169, 811
See application file for complete search history.

(56) References Cited

U.S. PATENT DOCUMENTS 5,821,073 A * 10/1998 Lee ............... 435/7.92

(Continued)

OTHER PUBLICATIONS

Reid, S.M; Ferrris, N.P; Bruning, A.; Hutchings, G.H.; Kowalska, Z.; and Akerblom, L. "Development of a rapid chromatographic strip test for the pen-side detection of foot-and-mouth disease virus antigen," Journal of Virological Methods. vol. 96 (2001) 189-202.*

(Continued)

*Primary Examiner*—Mark L Shibuya
*Assistant Examiner*—Jacqueline Diramio
(74) *Attorney, Agent, or Firm*—Fox Rothschild LLP; Gerard P. Norton; Shahnam Sharareh

(57) ABSTRACT

A rapid immunoassay method and apparatus for detecting foot and mouth disease virus are disclosed. The method and test device permit pen-side testing of animals and provide test results within a relatively short time period. In a preferred embodiment, the method and apparatus provide a means for differentiating between FMDV-infected and FMDV-vaccinated animals.

10 Claims, 27 Drawing Sheets

Schematic Diagram of an Assay
for Detection of FMDV Antibody

U.S. PATENT DOCUMENTS

| | | | |
|---|---|---|---|
| 6,048,538 A * | 4/2000 | Wang et al. | 424/216.1 |
| 6,107,021 A * | 8/2000 | Wang et al. | 435/5 |
| 2003/0143636 A1* | 7/2003 | Simonson et al. | 435/7.9 |
| 2003/0149259 A1* | 8/2003 | Callahan et al. | 536/24.32 |
| 2004/0058316 A1* | 3/2004 | Jensen et al. | 435/5 |
| 2006/0115896 A1* | 6/2006 | Wong et al. | 435/345 |

OTHER PUBLICATIONS

Samuel, A.R.; Knowles, N.J.; Samuel, G.D.; and Crowther, J.R. "Evaluation of a Trapping ELISA for the Differentiation of Foot-and-Mouth Disease Virus Strains Using Monoclonal Antibodies," Biologicals. vol. 19 (1991) 299-310.*

* cited by examiner

The genetic map and proteins expressed by FMDV

L (Protease)
1A
1B
1C
1D
2A
2B
2C
3A
3B
3C (Protease)
3D (RNA Polymerase)

polyprotein precursor

Foot-and-mouth disease virus complete genome

*Fig. 1*

Schematic Diagram of an Assay for Detection of FMDV Antibody

Fig. 3

FIG. 4  Synthetic oligonucleotides for VP1

SEQ ID NO: 1
TW97-1
ATCCAAGGATCCACCACCTCTGCGGGTGAGTCTGCGGACCCGGTGACTGCCACCGTTGAGAAC

SEQ ID NO: 2
TW97-2
CCGTGTGCTGGCGACGCTGAACTTGGGTCTCACCACCGTAGTTCTCAACGGTGGCAGTCAC

SEQ ID NO: 3
TW97-3
TCAGCGTCGCCAGCACACGGACAGCGCGTTCATCTTGGACCGTTTCGTGAAAGTTAAGCC

SEQ ID NO: 4
TW97-4
CAGGGATCTGCATCAGGTCCAACACATTAACTTGTTCCTTTGGCTTAACTTTCACGAAACGG

SEQ ID NO: 5
TW97-5
TGGACCTGATGCAGATCCCTGCCCACACCTTGGTAGGTGCGCTCCTGCGTACGGCCACCTACT

SEQ ID NO: 6
TW97-6
TCGCCCTCGTGCTTAACGGCCAGCTCCAGGTCAGAGAAGTAGTAGGTGGCCGTACGCAGG

SEQ ID NO: 7
TW97-7
GCCGTTAAGCACGAGGGCGATCTCACCTGGGTTCCAAACGGCGCCCCTGAGACCGCACTGGA

SEQ ID NO: 8
TW97-8
GAGCGGTTCCTTGTGGTAAGCGGTTGGGTTGGTAGTGTTGTCCAGTGCGGTCTCAGGGGC

SEQ ID NO: 9
TW97-9
CTTACCACAAGGAACCGCTCACCCGTCTGGCGCTGCCTTACACGGCTCCACACCGTGTTTTAGC

SEQ ID NO: 10
TW97-10
TGCTGGTGTCACCGTACTTGCTGCTACCGTTGTAAACGGTCGCTAAAACACGGTGTGGAGCC

SEQ ID NO: 11
TW97-11
CAAGTACGGTGACACCAGCACTAACAACGTGCGTGGTGACCTGCAAGTGTTAGCTCAGAAGG

SEQ ID NO: 12
TW97-12
GATGGCACCGAAGTTGAAGGAGGTAGGCAGAGTACGTTCTGCCTTCTGAGCTAACACTTGCAGG
T

SEQ ID NO: 13
TW97-13
TCCTTCAACTTCGGTGCCATCAAGGCAACTCGTGTTACTGAACTGCTCTACCGTATGAAGCG

SEQ ID NO: 14
TW97-14
TTGAATGGCGAGCAGCGGACGCGGACAGTAGGTCTCGGCACGCTTCATACGGTAGAGCAG

SEQ ID NO: 15
TW97-15
GTCCGCTGCTCGCCATTCAACCGAGCGACGCTCGTCACAAGCAGCGTATTGTGGCACCGG

SEQ ID NO: 16
TW97-16
GCCTATGAATTCTTACAGCAGCTGTTTTGCCGGTGCCACAATACGCTGCT

Fig 5. Plasmid map of pBM-VP1Tw97F

FIG. 6  Synthetic oligonucleotides for 2C

SEQ ID NO: 17
2C-1
GCAGGATCCG ACGACGACGA CAAACTCAAA GCACGTGACA TCAACGACAT ATTTGCCGTT CT

SEQ ID NO: 18
2C-2
TTGCTGTATA AACGGCAAGA ATTCTTGCCA CTCACCGACC AGTTTGACTA GGACCGGTAG

SEQ ID NO: 19
2C-3
TCAAACTGAT CCTGGCCATC CGCGACTGGA TTAAGGCATG GATCGCCTCA GAAGAGAAGT

SEQ ID NO: 20
2C-4
CTAGCGGAGT CTTCTCTTCA AACAGTGGTA CTGTCTGGAC CACGGACCGT AGGAACTTTC

SEQ ID NO: 21
2C-5
GTGCCTGGCA TCCTTGAAAG TCAACGGGAT CTCAATGACC CCGGCAAATA CAAGGAGGCC

SEQ ID NO: 22
2C-6
GGCCGTTTAT GTTCCTCCGG TTCCTTACCG ACCTGTTGCG CGCAGTTCGC ACAAACTTCT

SEQ ID NO: 23
2C-7
GCGTCAAGCG TGTTTGAAGA GCGGGAACGT GCACATTGCC AATCTGTGTA AAGTGGTCGC

SEQ ID NO: 24
2C-8
TTAGACACAT TTCACCAGCG AGGCCGCGGG TCGTTCAGCT CTGGGCTTGG TCACCAGCAC

SEQ ID NO: 25
2C-9
GACCCGAACC AGTGGTCGTG TGCCTTCGCG GCAAATCCGG CACAAGGAAA AGCATCCTCG

SEQ ID NO: 26
2C-10
GTGTTCCTTT TCGTAGGAGC GCTTGCACGA GCGCGTCCGT TAAAGGTGTG TGAAGTGACC

SEQ ID NO: 27
2C-11
ATTTCCACAC ACTTCACTGG TAGGACCGAC TCGGTCTGGT ACTGCCCGCC CGACCCTGAC

SEQ ID NO: 28
2C-12
TGACGGGCGG GCTGGGACTG GTGAAACTGC CAATGTTAGT CGTCTGGCAG CAGCACTACC

SEQ ID NO: 29
2C-13
GCAGACCGTC GTCGTGATGG ACGACTTGGG CCAAAACCCA GACGGCAAAG ACTTCAAGTA

SEQ ID NO: 30
2C-14
CTGCCGTTTC TGAAGTTCAT GAAACGGGTT TACCAGAGGT GGTGCCCCAA GTAGGGCGGA

SEQ ID NO: 31
2C-15
CCACGGGGTT CATCCCGCCT ATGGCCTCGC TCGAGGATAA GGGTAAACCC TTCAACAGCA

SEQ ID NO: 32
2C-16
CCCATTTGGG AAGTTGTCGT TCCAGTATTA TCGATGTTGG TTGGACATGA GCCCTAAGTG

SEQ ID NO: 33
2C-17
AACCTGTACT CGGGATTCAC CCCAAAGACC ATGGTGTGCC CCGATGCGCT TAACCGGAGG

SEQ ID NO: 34
2C-18
GGCTACGCGA ATTGGCCTCC AAAGTGAAAC TGTAGCTGCA CTCGCGGTTT CTGCCCATGT

SEQ ID NO: 35
2C-19
GAGCGCCAAA GACGGGTACA AGATCAACAA CAAACTGGAC ATAGTCAAAG CACTTGAAGA

SEQ ID NO: 36
2C-20
TATCAGTTTC GTGAACTTCT GTGGGTGCGA TTGGGCCACC GCTACAAGGT TATGCTGACG

SEQ ID NO: 37
2C-21
CGATGTTCCA ATACGACTGC GCTCTTCTCA ACGGAATGGC CGTTGAAATG AAGAGAATGC

SEQ ID NO: 38
2C-22
GCAACTTTAC TTCTCTTACG TCGTTCTGTA CAAGTTCGGA GTTGGTGGGA AGGTCTTGTA

SEQ ID NO: 39
2C-23
CAACCACCCT TCCAGAACAT CTACCAGCTC GTTCAGGAGG TGATTGAGCG GGTGGAACTA

SEQ ID NO: 40
2C-24
ACTAACTCGC CCACCTTGAT GTGCTTTTCC ACAGCTCGGT GGGCTATAAA TTTGTC

SEQ ID NO: 41
2C-25
GTCGAGACCCGAACCAGTGGTCGTGTGCCT

SEQ ID NO: 42
2C-26
AGGCACACGACCACTGGTTCGGGTCTCGAC

Fig 7. Plasmid map of pBM-2CTw97F
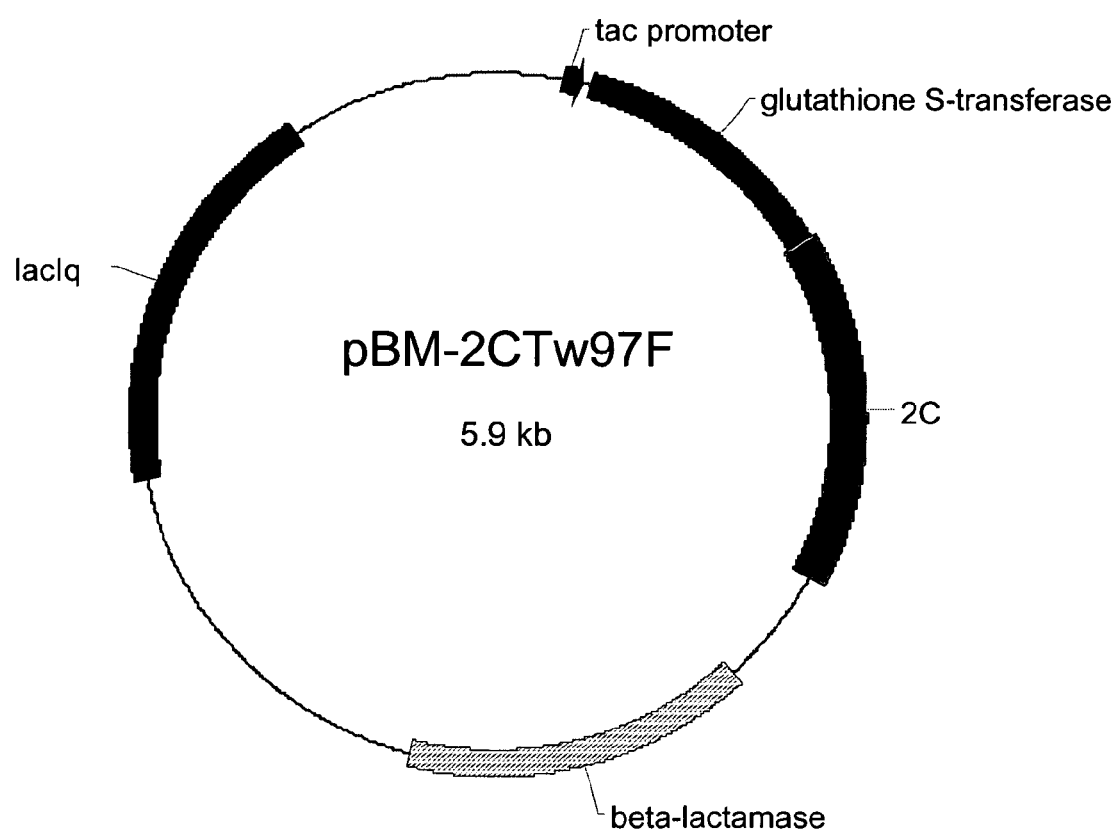

FIG. 8   Synthetic oligonucleotides for 3ABC

SEQ ID NO: 43
3ABC-1
GCAGGATCCG ACGACGACGA CAAAATTTCA ATCCCTTCCC AGAAGTCCGT GTTGTACT

SEQ ID NO: 44
3ABC-2
GGTCTTCAGG CACAACATGA AGGAGTAACT CTTCCCAGTC GTGCTTCGTC GCTAGCTCAA

SEQ ID NO: 45
3ABC-3
CACGAAGCAG CGATCGAGTT CTTCGAGGGG ATGGTCCACG ATTCCATCAA AGAGGAACTC

SEQ ID NO: 46
3ABC-4
TAAGGTAGTT TCTCCTTGAG GCTGGGGAGT AAGTCGTCTG GAGCAAGCAT TTTGCGCGGA

SEQ ID NO: 47
3ABC-5
CTCGTTCGTA AAACGCGCCT TCAAGCGCCT GAAAGAGAAC TTTGAAGTTG TAGCCCTGTG

SEQ ID NO: 48
3ABC-6
AAACTTCAAC ATCGGGACAC AAACTGGGAG AACCGTTTGT ATCACTAATA CGAGGCGGTT

SEQ ID NO: 49
3ABC-7
TAGTGATTAT GCTCCGCCAA GCGCGCAAGA GGTACCAATC GGTGGATGAC CCACTGGACG

SEQ ID NO: 50
3ABC-8
CCACCTACTG GGTGACCTGC CGCTGCATCG AGAACCGCTG CGCCTTTTCT TGGGAGACCT

SEQ ID NO: 51
3ABC-9
GCGGAAAAGA ACCCTCTGGA GACGAGTGCC GCTAGCGCTG TCGGTTTCAG AGAGAGATCC

SEQ ID NO: 52
3ABC-10
AGCCAAAGTC TCTCTCTAGG GGGTGGCTCG TTCCCTGCGC GCTTCTGCGC TTGCGACTCG

SEQ ID NO: 53
3ABC-11
CGAAGACGCG AACGCTGAGC CCGTCGTGTT CGGTAGGGAA CAACCGCGAG CTGAAGGACC

SEQ ID NO: 54

3ABC-12
GTTGGCGCTC ATGCGGCCGG GTTACCTCTC TGTCTTTGGC GATTTCCACT TTCGTTTTCG

SEQ ID NO: 55
3ABC-13
GTCAGAAACC TCTTAAAGTG AAAGCCGAGC TGCCACAACA GGAGGGACCA TACGCCGGCC

SEQ ID NO: 56
3ABC-14
GCTTTTGCTTTCACCTTTAGCGGTTTCTGTCTCTCCATTGGGCCGGCGTATGGTCCCTCC

SEQ ID NO: 57
3ABC-15
CTAAAGGTGA AAGCAAAAGC CCCCGTCGTG AAGGAAGGAC CTTACGAGGG ACCGGTGAAG

SEQ ID NO: 58
3ABC-16
GAATGCTCCC TGGCCACTTC TTTGGACAGC GAAATTTTCA CTTTCGTTTC TTGAACTATC

SEQ ID NO: 59
3ABC-17
GAAAGCAAAG AACTTGATAG TCACTGAGAG TGGTGCGCCA CCGACCGACT TGCAAAAGAT

SEQ ID NO: 60
3ABC-18
GGCTGGCTGA ACGTTTTCTA CCAGTACCCG TTGTGATTCG GTCAGCTCGA GTAGGAGCTG

SEQ ID NO: 61
3ABC-19
CAGTCGAGCT CATCCTCGAC GGCAAGACGG TAGCCATTTG CTGTGCTACC GGAGTGTTCG

SEQ ID NO: 62
3ABC-20
GACACGATGG CCTCACAAGC CGTGACGGAT GGAGCACGGA GCAGTAGAGA AGCGCCTTTT

SEQ ID NO: 63
3ABC-21
CGTCATCTCT TCGCGGAAAA GTACGACAAG ATCATGTTGG ACGGCAGAGC CTTGACAGAC

SEQ ID NO: 64
3ABC-22
TGCCGTCTCG GAACTGTCTG TCACTGATGT CTCACAAACT CAAACTCTAA TTTCATTTTC

SEQ ID NO: 65
3ABC-23
GTTTGAGATT AAAGTAAAAG GACAGGACAT GCTCTCAGAC GCCGCTCTCA TGGTGTTGCA

SEQ ID NO: 66
3ABC-24

CGGCGAGAGT ACCACAACGT GGCACCCTTA GCGCACGCAC TGTAGTGCTT TGTGAAAGCA

SEQ ID NO: 67
3ABC-25
ACATCACGAA ACACTTTCGT GACGTAGCGA GAATGAAGAA GGGAACCCCC GTCGTCGGTG

SEQ ID NO: 68
3ABC-26
CCCTTGGGGG CAGCAGCCAC ACTAGTTGTT ACGACTGCAG CCCTCTGAGT ATAAGAGACC

SEQ ID NO: 69
3ABC-27
GGGAGACTCA TATTCTCTGG TGTAGCCCTC ACTTACAAGG ACATCGTCGT GTGTATGGAT

SEQ ID NO: 70
3ABC-28
TGTAGCAGCA CACATACCTA CCTCTGTGGT ACGGACCCGA GAAACGGATG TCCCGTAGGT

SEQ ID NO: 71
3ABC-29
CTTTGCCTAC AGGGCATCCA CCAAGGCAGG CTACTGCGGA GGAGCCGTCC TGGCAAAGGA

SEQ ID NO: 72
3ABC-30
CCTCGGCAGG ACCGTTTCCT GCCCCGGCTT TGCAAGTAGC AACCGTGGGT GAGGCGTCCA

SEQ ID NO: 73
3ABC-31
TTGGCACCCA CTCCGCAGGT GGAAACGGCA TAGGATACTG TTCGTGTGTT TCCCGATCAA

SEQ ID NO: 74
3ABC-32
AAGCACACAA AGGGCTAGTT ACGAGGACTT CTACTTCCGT GTGTAGCTGG GACTTGGTGT

SEQ ID NO: 75
3ABC-33
TGCAAGCTTT TACTCGTGGTGTGGTTCAGGGTCGATGTGTGCCTTCATC

SEQ ID NO: 76
3ABC-34
CTTTAAAAGTGAAAGCAAAGAACTTGATAGTCACT

SEQ ID NO: 77
3ABC-35
AGTGACTATCAAGTTCTTTGCTTTCACTTTTAAAG

SEQ ID NO: 78
3ABC-36
CCGTCGTGTTCGGTAGGGAA

SEQ ID NO: 79
3ABC-37
AAAGTAAAAGGACAGGACAT

Fig 9. Plasmid map of pBM-3ABCTw97F
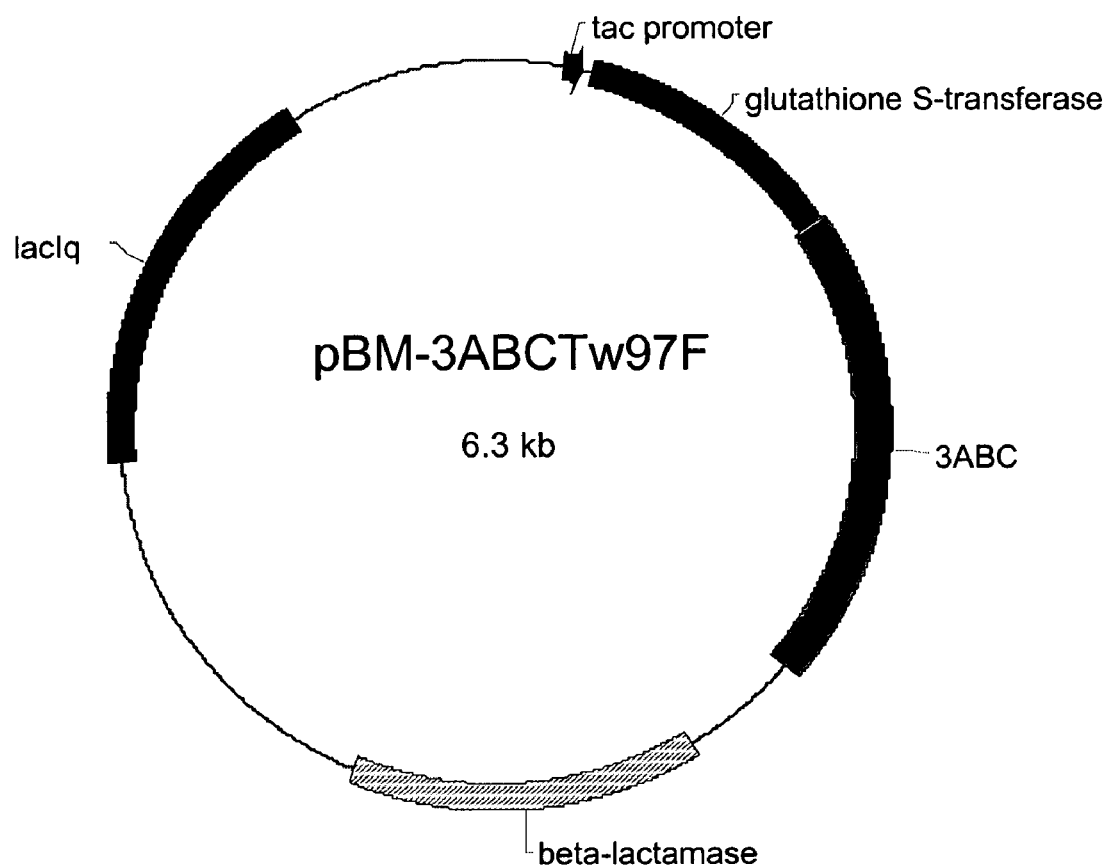

FIG. 10  Synthetic oligonucleotides for 3D

SEQ ID NO: 80
3d-1A
GCTATC GGATCC GGGTTGATCG TTGATACCAG AGATGTGGAA

SEQ ID NO: 81
3d-2
TGGGTGCAAGCTTGGTTTTGCGCATTACATGGACGCGCTCTTCCACATCTCTGGTATCAA

SEQ ID NO: 82
3d-3
CAAAACCAAGCTTGCACCCACCGTCGCGCACGGTGTGTTCAATCCTGAGTTCGGGCCTGC

SEQ ID NO: 83
3d-4
AACACCTTCGTTCAGACGTGGGTCCTTGTTAGACAAGGCGGCAGGCCCGAACTCAGGATT

SEQ ID NO: 84
3d-5
CACGTCTGAACGAAGGTGTTGTCCTCGATGAAGTCATTTTCTCCAAGCATAAAGGAGACA

SEQ ID NO: 85
3d-6
CAGCGGCGGAACAGCGCTTTGTCCTCCTCAGACATCTTTGTGTCTCCTTTATGCTTGGAG

SEQ ID NO: 86
3d-7
AAAGCGCTGTTCCGCCGCTGCGCTGCTGACTACGCGTCACGCCTGCACAGTGTGCTGGGT

SEQ ID NO: 87
3d-8
CCTTGATTGCCTCGTAAATGCTCAGTGGGGCATTTGCCGTACCCAGCACACTGTGCAGGC

SEQ ID NO: 88
3d-9
CATTTACGAGGCAATCAAGGGCGTTGACGGACTCGACGCCATGGAGCCAGACACCGCACC

SEQ ID NO: 89
3d-10
TGCACCGCGGCGTTTCCCCTGGAGGGCCCAGGGAAGGCCAGGTGCGGTGTCTGGCTCCAT

SEQ ID NO: 90
3d-11
AGGGGAAACGCCGCGGTGCACTTATCGATTTCGAGAACGGCACGGTCGGACCCGAGGTTG

SEQ ID NO: 91
3d-12

AACTTGTATTCTCTTTTCTCCATGAGCTTCAAGGCAGCCTCAACCTCGGGTCCGACCGTG

SEQ ID NO: 92
3d-13
GAGAAAAGAGAATACAAGTTTGTTTGCCAGACCTTCCTGAAGGACGAAATTCGCCCGATG

SEQ ID NO: 93
3d-14
AAACGTCGACAATGCGAGTCTTGCCGGCACGTACTTTCTCCATCGGGCGAATTTCGTCCT

SEQ ID NO: 94
3d-15
GACTCGCATTGTCGACGTTTTGCCTGTTGAACACATTCTTTACACCAGGATGATGATTGG

SEQ ID NO: 95
3d-16
CTGCGGCCCGTTGTTTGAGTGCATTTGTGCACAAAATCTGCCAATCATCATCCTGGTGTA

SEQ ID NO: 96
3d-17
ACTCAAACAACGGGCCGCAGATTGGCTCAGCGGTCGGTTGCAACCCTGATGTTGATTGGC

SEQ ID NO: 97
3d-18
CACACGTTTCTGTATTGGGCGAAGTGTGTGCCGAATCTCTGCCAATCAACATCAGGGTTG

SEQ ID NO: 98
3d-19
GCCCAATACAGAAACGTGTGGGACGTGGACTATTCGGCCTTTGATGCAAACCACTGCAGC

SEQ ID NO: 99
3d-20
CCGTGCGGAACACCTCTTCAAACATGATGTTCATGGCATCGCTGCAGTGGTTTGCATCAA

SEQ ID NO: 100
3d-21
TGAAGAGGTGTTCCGCACGGAGTTCGGCTTCCACCCGAATGCTGAGTGGATTCTGAAGAC

SEQ ID NO: 101
3d-22
GATGCGCTTGTTCTCATAGGCGTGTTCCGTGTTCACGAGAGTCTTCAGAATCCACTCAGC

SEQ ID NO: 102
3d-23
CCTATGAGAACAAGCGCATCACTGTTGAAGGCGGGATGCCATCTGGCTGTTCCGCAACAA

SEQ ID NO: 103
3d-24
TAGAGCACGTAGATGTTATTCAAAATTGTGTTGATGATGCTTGTTGCGGAACAGCCAGAT

SEQ ID NO: 104
3d-25
AATAACATCTACGTGCTCTACGCCTTGCGTAGACACTATGAGGGGGTTGAGCTGGACACC

SEQ ID NO: 105
3d-26
TTGCCACCACGATGTCGTCTCCATAGGAGATCATGGTGTAGGTGTCCAGCTCAACCCCCT

SEQ ID NO: 106
3d-27
AGACGACATCGTGGTGGCAAGCGATTATGATCTGGACTTTGAGGCCCTCAAGCCTCACTT

SEQ ID NO: 107
3d-28
GCTTTTGTCAGCTGGAGTAATGGTTTGGCCAAGAGATTTGAAGTGAGGCTTGAGGGCCTC

SEQ ID NO: 108
3d-29
TTACTCCAGCTGACAAAAGCGACAAAGGTTTTGTTCTTGGTCACTCCATTACTGACGTCA

SEQ ID NO: 109
3d-30
CCAGTGCCATAATCCATGTGGAAGTGTCTTTTGAGGAAAGTGACGTCAGTAATGGAGTGA

SEQ ID NO: 110
3d-31
CACATGGATTATGGCACTGGGTTTTACAAACCTGTGATGGCCTCGAAGACCCTCGAGGCT

SEQ ID NO: 111
3d-32
ACTTCTCCTGGATGGTCCCACGGCGTGCAAAGGAGAGGATAGCCTCGAGGGTCTTCGAGG

SEQ ID NO: 112
3d-33
TGGGACCATCCAGGAGAAGTTGATTTCCGTGGCAGGACTCGCCGTCCACTCCGGACCAGA

SEQ ID NO: 113
3d-34
AAAGAGGCCCTGGAAGGGCTCAAAGAGACGCCGGTACTCGTCTGGTCCGGAGTGGACGGC

SEQ ID NO: 114
3d-35
AGCCCTTCCAGGGCCTCTTTGAGATTCCAAGCTACAGATCACTTTACCTGCGTTGGGTGA

SEQ ID NO: 115
3d-36A
GCAATCGAATTCTTATGCGTCGCCGCACACGGCGTTCACCCAACGCAGGTAAAGT

SEQ ID NO: 116
pGEX5
CTGGCAAGCCACGTTTGGTG

SEQ ID NO: 117
pGEX3
GGAGCTGCATGTGTCAGAGG

Fig 11. Plasmid map of pBM-3Df
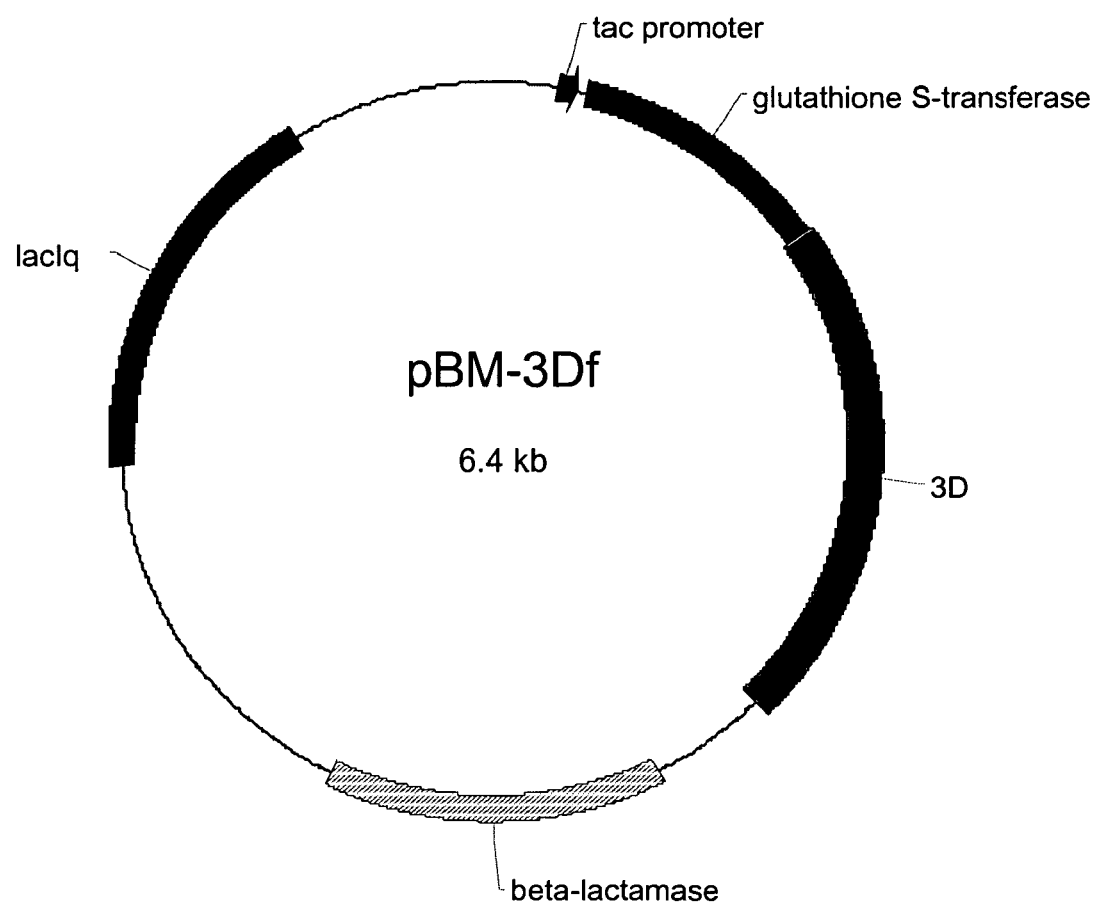

Fig. 12. One-line Test Kit Configuration

T : 2C or 3ABC
C : Control (−) NAÏVE or VACCINATED (+++) INFECTED

Fig. 13 Two-line Test Kit Configuration

INFECTED     VACCINATED     NAIVE

T1: VP1 or 3D, T2: 2C or 3ABC, C: Control

Comparison of 3ABC ELISA and Pen-side Test

FMDV Infected Bovine #19

3ABC ELISA: Cutoff Value = 10, Pen-side Test: Positive (+) Negative = (−)

Days Post Infection (DPI)

Fig. 14

Comparison of 3ABC ELISA and Pen-side Test

FMDV Infected Bovine #21

3ABC ELISA: Cutoff Value = 10, Pen-side Test: Positive (+) Negative = (−)

Days Post Infection (DPI)

Fig. 15

Comparison of 3ABC ELISA and Pen-side Test

FMDV Infected Swine #183

3ABC ELISA: Cutoff Value = 13, Pen-side Test: Positive (+) Negative (−)

Fig. 16

Comparison of 3ABC ELISA and Pen-side Test

FMDV Infected Swine #186

3ABC ELISA: Cutoff Value = 13, Pen-side Test: Positive (+) Negative (−)

Fig. 17

Comparison of 3ABC ELISA and Pen-side Test

FMDV Infected Swine #186

3ABC ELISA: Cutoff Value = 13, Pen-side Test: Positive (+) Negative = (■)

Fig. 18

METHOD AND DEVICES FOR RAPID DIAGNOSIS OF FOOT-AND-MOUTH DISEASE

FIELD OF THE INVENTION

The present invention relates to the field of immunology, and to a method of detecting antibodies to structural and/or non-structural proteins of animal foot-and-mouth disease virus and, more particularly, to provide a rapid, one step qualitative, sensitive, and specific immunochromatographic assay.

BACKGROUND OF THE INVENTION

Foot and mouth disease (FMD) is a devastating and extremely contagious disease of livestock. Its severity is such that the Office International des Epizooties has listed it as an A disease. All species of the order of Artiodactyla, such as, but not limited to, pig, hog, javelina, hippopotamus, camel, llama, mouse deer, giraffe, okapi, deer, pronghorn, antelope, cattle, goat, and sheep, are susceptible to infection with FMD. The financial losses due to infection from the FMD Virus (FMDV) are significant. For example, there are direct losses due to deaths in young animals, loss of milk and loss of meat, as well as decreases in product(s) yield. The costs associated with eradication of infected animals, as well as the costs required to limit the spread of FMDV to non-infected animals, are high. Additionally, there are indirect losses due to the imposition of trade restrictions.

The causative agent of FMD is foot-and-mouth disease virus (FMDV), an aphthovirus of the Picornaviridae family (Bittle et al., 1982 and Fross et al., 1984). The FMDV genome consists of a single RNA positive strand of approximately 8,000 nucleotide bases. The viral RNA is initially translated as a single polypeptide that is subsequently cleaved by viral-encoded proteases to produce four structural capsid proteins (VP1-VP4) and four non-structural proteins (2C, 3A, 3ABC and 3D). The coding region for structural and nonstructural proteins is shown schematically in FIG. 1.

FMDV is antigenically heterogeneous. Seven distinct serotypes have been recognized: O, A, C, ASIA1, SAT1, SAT2 and SAT3 (SAT=Southern African Territories). Each serotype of FMDV is antigenically distinct from the other six serotypes. Serotype A viruses are the most variable, having more than 30 subtypes. Furthermore, each serotype can be subdivided into antigenically distinct multiple subtypes. The serotypes of FMDV were originally identified by cross-immunity experiments in animals. Although an animal that has recovered from infection with one serotype is resistant to challenge by that same serotype, it still remains susceptible to infection by any of the other serotypes.

The different serotypes of FMDV are most prevalent in certain geological areas. For instance, in Asia serotypes A, O, and ASIA1 are most common; in Europe and South America, serotypes A, O, and C are found; and in Africa, serotypes A, O, and SAT are prevalent.

Following infection with FMDV, specific antibodies (IgG and/or IgM, IgA) against the structural proteins (SPs) and non-structural proteins (NSPs) appear. The antibody titers rapidly increase over time and remain high. Thus, the presence of specific FMDV antibody in a sample indicates that the animal from which the sample was collected has had contact with FMDV or an antigen derived from FMDV (such as, but not limited to, animals that have been vaccinated).

Diagnosis of FMD

Primary diagnosis of FMDV commonly involves recognition of typical clinical signs in affected animals. Clinical signs of FMD are essentially similar in all species although the severity may vary considerably. The principal signs are pyrexia, followed by vesicle formation in the mouth and on the feet. Vesicle formation in the mouth causes the animals to salivate. The vesicle formation on the feet causes lameness.

Serological diagnosis of FMD is determined by the presence of FMDV-specific antigens or antibodies in animals suspected of having been infected. The current method of detection is by an enzyme-linked immunosorbent assay (ELISA) or by a virus neutralization test. These methods require multiple steps, are time consuming, and are tedious to perform. Additionally, these assays require long incubation times, resulting in a significant delay in the diagnosis. Time is critical, as FMD is highly contagious. Thus any delay in diagnosis will result in the rapid spread of the disease to uninfected animals, causing a greater loss in product, and subsequently a greater financial loss.

The invention presented herein overcomes these insufficiencies by providing a rapid, one-step method of detecting antibodies and/or antigens in a fluid sample from an animal suspected of having been infected. Additionally, the method presented herein allows for the rapid determination of protection from infection in those animals that have been vaccinated. Furthermore, the disclosed invention is able to determine if an animal has been exposed to FMDV, either by infection or by vaccination, within 30 minutes.

Clinical Symptoms of FMD are not a Reliable Indicator of FMDV Infection

The invention provided herein allows for the rapid detection of antibody to FMDV. Vesicular material is not always available from animals that have been infected with FMDV, thus an additional advantage provided by the present invention is that a liquid sample from animals suspected of having been exposed to FMDV are diagnosed within 30 minutes. Current methodology requires multiple steps (each of which is a potential source of error) and days of incubation(s) prior to obtaining a result. Additionally, diagnosis of FMD by clinical signs alone is difficult, especially for sheep and goats, in which clinical signs are often mild (Barnett, P. V et al., 1999 and Callens, M., K. et al., 1998). Furthermore, several other vesicular virus infections, including, but not limited to, those caused by swine vesicular disease (SVD) virus and vesicular stomatitis virus (VSV), cannot be distinguished from FMDV infection by the clinical findings. Thus, a rapid diagnosis of the infectious agent is critical.

Moreover, FMDV can establish a persistent or carrier stage in ruminants in the absence of any clinical manifestation of the disease. Such carrier animals are a source of new outbreaks of the disease. Therefore, there is a long sought, yet unfulfilled, need for a rapid serological method in which infected and/or asymptomatic carrier animals are identified. Additionally, there is a long sought, yet unfulfilled, need for an assay system that will distinguish between animals that are protected from FMDV infection, i.e., those that have been vaccinated, from animals that have been infected with FMDV. Since both vaccination against FMDV and FMDV infection induced antibodies to the structural capsid proteins, assays that detect the structural capsid protein alone are insufficient to differentiate vaccinated animals from those that have been infected. Thus, antibodies against structural proteins can only be used in vaccine-free regions, such as, but not limited to, the USA or the UK. Assay systems that can only detect these anti-structural protein antibodies are therefore not useful in regions where animals are vaccinated. Since unvaccinated animals present in the geographic regions where vaccinations are given remain susceptible to infection with FMDV, there is a long sought, yet unfulfilled, need for a diagnostic test that will differentiate an infected animal from one that has been vaccinated (and thus protected from infection). The invention disclosed herein provides such an assay system.

The present invention further provides an assay system that will measure the efficacy of vaccinations. The present invention disclosed herein provides for the current deficiencies in the art by providing an assay system that allows for the rapid detection of antibodies to both SPs and NSPs, thereby allowing for vaccinated animals to be differentiated from those that are infectious. Finally, the present invention provides a detection method that allows for rapid analysis of the geographic distribution of specific FMDV serotypes and/or serotype subtypes for epidemiological studies.

Thus the present invention provides a rapid immunochromatographic assay wherein *E. coli*-expressed recombinant FMDV structural and non-structural proteins are incorporated into a solid support for the capture of antibodies to FMDV in animal body fluids. The immunochromatographic assay disclosed herein allows for the diagnosis of FMDV infection, for the identification of FMDV carriers, as well as for the ability to differentiate between an infected animal and an animal that has been vaccinated (and thus protected from FMDV).

Abbreviations

"SP" means "structural protein or structural capsid protein
"NSP" means "non-structural protein"
"FMD" means "foot-and-mouth disease"
"FMDV" means "foot-and-mouth disease virus"
"ELISA" means "enzyme linked immunosorbent assay"
"PBS" means "phosphate buffered saline"
"PCR" means "polymerase chain reaction"
"PMSF" means "phenyl methyl sulfonyl fluoride"
"BSA" means "bovine serum albumin"
"Tris-HCl" means "tris(hydroxymethyl)aminomethane-hydrochloride"
"EDTA" means "ethylenediaminetetraacetic acid"
"IPTG" means "isopropylthiogalactoside"
"SDS-PAGE" means "sodium dodecyl sulfate-polyacrylamide gel electrophoresis"
"RT-PCR" means "reverse transcription-polymerase chain reaction"
"IgG" means "Immunoglobulin G"
"IgM" means "Immunoglobulin M"
"LB" means "Luria-Bertani"
"DTT" means "dithiothreitol Definitions "TE" is 10 mM Tris-HCl, pH 8.0 (Sigma-Aldrich) and 1 mM EDTA, pH 8.0 (Sigma-Aldrich)"

"Body fluid" is any substance that emanates or derives from the body, including but not limited, to blood, urine, tears, saliva, and breast milk.

"Analyte" is the substance to be detected which may be present in the test sample. The analyte can be any substance for which there exists a naturally occurring specific binding member (such as, but not limited to, an antibody), or for which a specific binding member can be prepared. Thus, an analyte is a substance that can bind to one or more specific binding members. Analytes include, but are not limited, to antigenic substances, haptens, antibodies, and combinations thereof.

"Labels" for use in the present invention can include, but are not limited to, chromogens; catalysts; fluorescent compounds; chemiluminescent compounds; radioactive elements; colloidal metallic (such as gold), non-metallic (such as selenium) and dye particles; enzymes; enzyme substrates; organic polymer latex particles, liposomes or other vesicles containing such signal producing substances; etc. A large number of enzymes suitable for use as labels include, but are not limited to, phosphatases and peroxidases, such as alkaline phosphatase and horseradish peroxidase which are used in conjunction with enzyme substrates, such as nitro blue tetrazolium, 3,5',5,5'-tetranitrobenzidine, 4-methoxy-1-naphthol, 4-chloro-1-naphthol, 5-bromo-4-chloro-3-indolyl phosphate, chemiluminescent enzyme substrates such as the dioxetanes, and derivatives and analogs thereof. Fluorescent compounds such as fluorescein, phycobiliprotein, rhodamine and the like, including their derivatives and analogs are suitable for use as labels.

"Capture reagent" refers to an unlabeled specific binding member which is specific either for the analyte, for the indicator reagent, or for an ancillary specific binding member. The capture reagent can be directly or indirectly bound to a solid phase material before the performance of the assay or during the performance of the assay, thereby enabling the separation of immobilized complexes from the test sample.

"Specific binding member" or "specific binding agent" or "labeled binding partner" refers to one member or partner of a specific binding pair. A "specific binding pair" or "specific binding complex" refers to two different molecules wherein one of the molecules, through chemical or physical means, specifically binds to the second molecule. A typical example of specific binding members or agents which constitute a specific binding pair are an antigen and an antibody. Other specific binding pairs include, but are not limited to, biotin and avidin, protein G and/or A and immunoglobulin, carbohydrates and lectins, cofactors and enzymes, enzyme inhibitors and enzymes, effector and receptor molecules, and the like. Furthermore, specific binding pairs can include members that are analogs of the original specific binding members, for example, an analyte-analog. Immunoreactive specific binding members include antigens, antigen fragments, antibodies, antibody fragments, both monoclonal and polyclonal, and complexes thereof.

"Signal producing system" refers to a system that has at least two members: a catalytic member and a solute, which undergoes a reaction catalyzed by the catalytic member, which leads directly or indirectly to a product on or in the surface which provides a detectible signal. The catalytic member may be enzymatic or non-enzymatic. The solute is any compound which is capable of undergoing a reaction catalyzed by a catalytic member of the signal producing system, which reaction results either directly or indirectly in a detectible signal generating compound. The signal-generating compound will provide a spectrophotometric or visible signal, an electrochemical signal or an electronically detectible signal. The observed detectible signal is related to the amount of catalyst bound through the binding of the catalyst-bound-analyte, which in turn is related to the amount of analyte in the test sample.

"Ancillary reagent" refers to an additional reagent(s) included in the assay. Ancillary reagents include, but are not limited to, enzyme substrates, cofactors, activators, scavengers, inhibitors or the like. In addition, buffers will normally be present, as well as stabilizers. Frequently in addition to these additives, additional proteins may be included, such as albumins; or surfactants, particularly non-ionic surfactants, e.g. polyalkylene glycols, or the like.

BRIEF DESCRIPTION OF THE DRAWINGS

FIG. 1 is a schematic diagram of the genetic map of FMDV RNA and proteins.

FIG. 3 is a schematic diagram of an assay for the detection of antibody in the sample.

FIG. 4 is the nucleotide and amino acid sequence of the VP-1 protein.

FIG. 5 is the plasmid map of pBM-VP1Tw97F.

FIG. 6 is the nucleotide and amino acid sequence of the 2C protein FIG. 7 is the plasmid map of pBM-2CTw97F FIG. 8 is the nucleotide and amino acid sequence of the 3ABC protein FIG. 9 is the plasmid map of pBM-3ABCTw97F FIG. 10 is the nucleotide and amino acid sequence of the 3D protein FIG. 11 is the plasmid map of pBM-3DTw97F FIG. 12 is a schematic diagram of the test kit formulation.

FIG. 13 is a schematic diagram of the two-line test kit configuration.

FIG. 14 is a chart comparing test results over time of a 3ABC ELISA and the test of the presenting invention for an FMDV-infected cow.

FIG. 15 is a chart comparing test results over time of a 3ABC ELISA and the test of the presenting invention for a second FMDV-infected cow.

FIG. 16 is a chart comparing test results over time of a 3ABC ELISA and the test of the presenting invention for an FMDV-infected pig.

FIG. 17 is a chart comparing test results over time of a 3ABC ELISA and the test of the presenting invention for a second FMDV-infected pig.

DETAILED DESCRIPTION OF THE INVENTION

The Test Device

Figure 2:
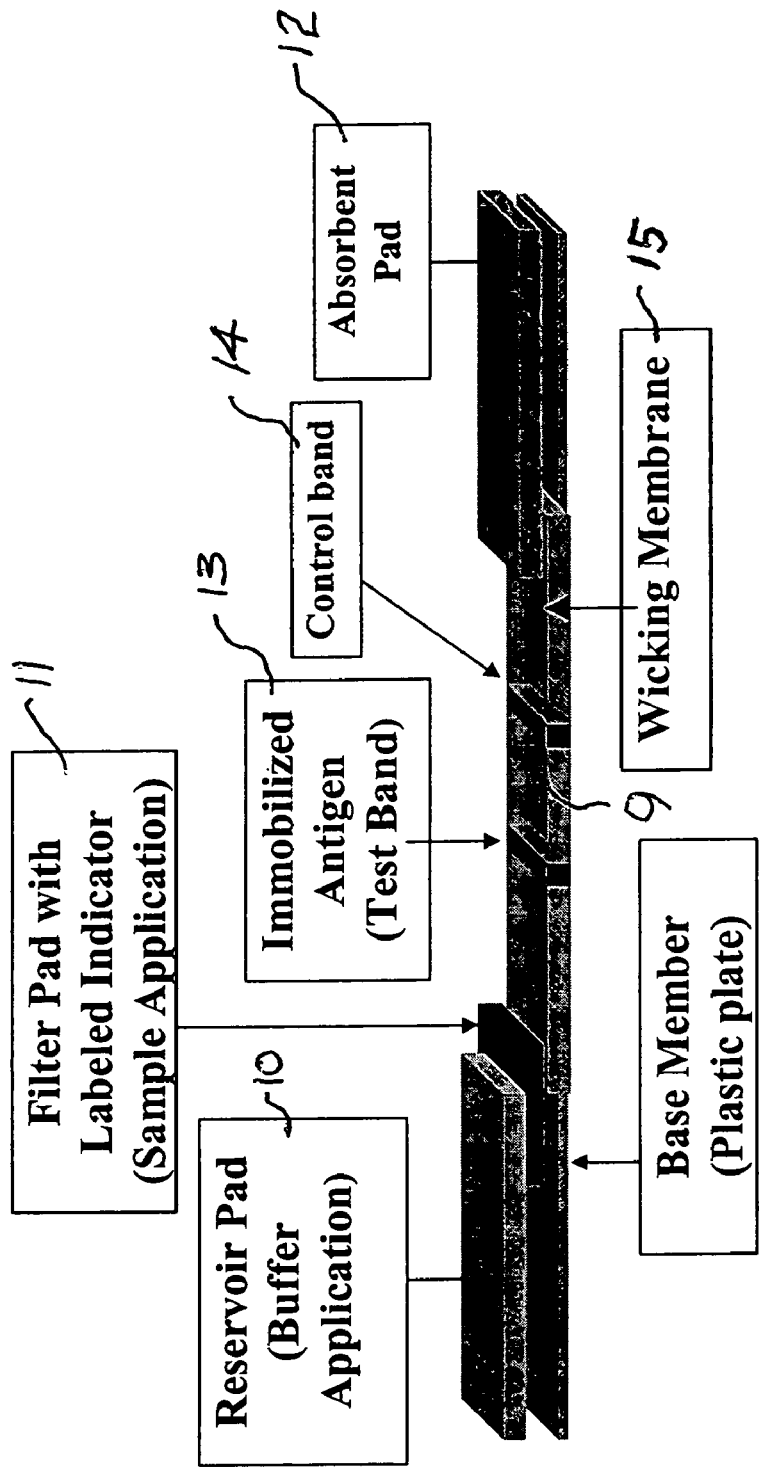
FIG. 2 is an elevation view of the strip configuration of the assay device.

The present invention relates to a device for the detection of an analyte in a sample of biological fluid through the use of immunochemical ligand-receptor reactions and specially selected, treated, and arranged filter materials (FIG. 2; see also U.S. Pat. No. 5,559,041 which is hereby incorporated by reference). The present invention includes a non-reactive cover (also referred to as an enclosure or casing) around the device. The cover encloses at least the strip to avoid contact with, and contamination of, the capture sites. In one embodiment, the cover also includes a raised area adjacent to the application pad to facilitate receiving and/or containing a certain volume of the test sample and/or wicking solution. In a further embodiment of the invention, the cover includes a cut out area or areas in the form of a letter, number, icon, or symbol or any combination thereof. In this embodiment, the cut out area or areas form the design for a particular capture site(s) once the strip is completely enclosed. In another embodiment of the invention, a sufficient portion of the strip is encased to prevent the applied test sample from contacting the capture sites without first passing through a portion of the strip.

The Application Pad

It is contemplated and within the scope of the present invention that the solid phase can be any suitable porous material with sufficient porosity to allow access by detection antibodies and/or antigens and a suitable surface affinity to bind antigens and/or antibodies. Microporous structures, in general, are preferred, but materials with gel structure in the hydrated state may be used as well. Such useful solid supports include, but are not limited to, nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), porous polyethylene frit or pads, and glass fiber filter paper; either used by themselves or in conjunction with other materials.

The surface of such supports may be activated by chemical processes that cause covalent linkage of the antigen and/or antibody to the support. Alternatively, the irreversible binding of the antigen and/or antibody is obtained by adsorption on the porous material by poorly understood hydrophobic forces. Other suitable solid supports are well known to those of skill in the art. It is also well known in the art that the material chosen for the solid support(s) is one that is compatible with the analyte and assay reagents used.

2 Pad System/3 Pad System

The filter pad 11 is separate and distinct from said reservoir pad 10, and wicking membrane 15, and interposed between and contiguous with the wicking membrane 15, and the reservoir pad 10'(3 Pad system). Or one filter pad 11' functions as both reservoir 10' and filter zone (2 Pad system). The filter zone has impregnated therein a labelled immunochemical component capable of binding to an analyte of interest in sample to form an immuno-complex. The filter zone is operable to permit passage of any specific immuno-complex to the wicking membrane 15, while impeding passage of larger components then contained in the sample; and at least one immobilized substance disposed in at least one assay indicia zone 4 of the wicking membrane 15 downstream of the filter zone and defining assay indicia 13, the immobilized substance being operable to bind a specific immuno-complex contained in the sample to form the assay indicia 13.

Reagents are Incorporated within the Test Device

In addition, the application pad typically contains one or more assay reagents either diffusively or non-diffusively attached thereto. Reagents that are contained in the application pad include, but are not limited to, labeled reagents, ancillary specific binding members, and/or signal producing system components needed to produce a detectable signal. The isolation of assay reagents in the application pad also separates the interactive reagents, thereby facilitating the manufacturing process.

In an embodiment of the present invention, predetermined amounts of signal producing components and ancillary reagents are incorporated within the device, thereby avoiding the need for additional protocol steps or reagent additions. Thus, it also is within the scope of this invention to provide more than one reagent to be immobilized within the application pad and/or the strip material.

This invention covers detection method for FMDV antibody, PRRSV (Porcine Respiratory and Reproductive Symptom Virus) antibody and antigen, FeLV (Feline Leukemia Virus) antigen, FIV (Feline Immunodeficiency Virus) antibody, Mad Cow disease marker, CSF (Classical Swine Fever) antibody and antigen, *B. canis* (*Brucellocis canis*) antibody and antigen, Johnes disease antibody and BVDV (Bovine Viral Diarhrea Virus). Antigen. Also this invention covers detection of the cancer markers, hormones, enzyme and drugs, and antigens that may be applied as disease or biological makers.

Chromatographic Material Transports Liquids

The invention disclosed herein provides assay devices and methods wherein strips of chromatographic material capable of transporting liquids are used in the assay. In one embodiment of the present invention, the assay device includes test sample application pads that are in fluid flow contact with the strip which functions to regulate the flow of the test sample to the chromatographic material, to filter the test samples and to deliver and/or mix assay reagents. For example, not meant to limit the invention in any way, during a binding assay the labeled reagent is contained in the application pad and is released from the pad to the strip containing the applied test sample, thereby eliminating the need to combine the test sample and labeled reagent prior to using the device (FIG. 3).

In a further embodiment of the invention the assay reagents are incorporated within the chromatographic material, as well as in the application pad. By varying the configuration of reagent-containing sites on the device, qualitative and quantitative displays of assay results are obtained. The reagents are situated in the devices in such a way as to make the assay substantially self-performing and to facilitate the detection and quantitation of the assay results. Any signal resulting from the reaction(s) at the reagent-containing site(s) is detected by instrumentation or by direct visual observation.

Test Device For Diagnosis of FMD

In one embodiment the test device for the assay includes, but is not limited to, a nitrocellulose membrane strip upon which are placed, and allowed to dry in separate distinct capture areas, highly purified recombinant antigens derived from FMDV and/or specific monoclonal antibodies to FMDV (FIG. 2). The test device further includes a filter pad which contains a labeled indicator, such as gold colloid conjugated with protein G and/or A, suspended in a fluid containing nitrocellulose blocking proteins, which have been dried prior to assembly and affixed to the distal end of the nitrocellulose membrane (FIGS. 2 and 3). The entire device is held permanently in place by a top clear laminating material which bears an adhesive surface in contact with the top surface of the nitrocellulose membrane and attached to the conjugate pad, and a bottom laminating material which bears an adhesive surface in contact with the bottom surface of the nitrocellulose membrane. The fluid test sample flows from the distal end to the proximal end. In one embodiment of the device, there is a test sample pad and reactivity zone upon which the test sample is placed. The read out (in the capture areas and/or in the test sample reactivity zone) is either visual, without the aid of laboratory equipment, or automated. In a further embodiment of the invention, the test device is enclosed in a casing of molded plastic or other suitable material.

Analyte Detection

An exemplary embodiment of the present invention, which is not meant to define or constrain the invention described herein, is performed as follows. A test sample, such as, but not limited to, animal serum is contacted with the labeled indicator, such as protein G and/or protein A-gold conjugate, on the filter pad at the sample application point on the test device. IgG and/or IgM antibodies in the sample are bound by the protein G and/or protein A-gold conjugate and the protein G and/or protein A-gold conjugate—antibody complexes are chromatographed along the length of the absorbent pad (such as, but not limited to, a nitrocellulose membrane). As an internal control for efficacy, a labeled control reagent is also present in the filter pad. As the fluid, containing both the aforementioned complexes and the internal control reagent, flow, they pass over the line where the FMDV recombinant antigens have been applied in test band 13 (FIG. 3). If the complexes contain specific antibody (IgG and/or IgM) to the recombinant antigens in the test band 13, the antigens in the test band will form a complex with the protein G and/or A antibody complex and a detectable signal is generated. Simultaneously, the labeled control reagent present in the fluid will flow, via capillary action, to the control band 14 wherein an immobilized control capture reagent will bind to the labeled control reagent, generating a positive signal. A further embodiment of the invention disclosed herein incorporates the quantitation of the antibody and/or antigen in the test sample, as determined by the intensity of the signal generated relative to an intensity of signals generated in a standard curve.

EXAMPLES

Oligonucleotides for gene construction and sequencing were synthesized at ResGen (Huntsville, Ala.). Unless otherwise indicated, DNA sequencing was also performed at ResGen.

Polymerase Chain Reaction (PCR)

For PCR, Vent DNA polymerase and buffer were purchased from New England Biolabs, Inc. (Beverly, Mass.) and a mixture of dNTPs was purchased from Amersham-Pharmacia (Piscataway, N.J.) and used according to the manufacturer's specifications, unless otherwise indicated. PCR amplifications were performed on a GeneAmp 2400 thermal cycler from Perkin-Elmer Corporation (Foster City, Calif.). The PCR product was purified using Qiagen PCR spin column (Qiagen Inc., Chatsworth, Calif.), as recommended by the manufacturer. Unless indicated otherwise, restriction enzymes were purchased from New England BioLabs and DNA fragments were initially isolated on agarose (Sigma-Aldrich) gels prior to the restriction digestion for their cloning.

Isolation of the Desired Clone(s)

The desired fragment was excised and the DNA was extracted with a QIAEX II gel extraction kit, as recommended by the manufacturer. DNA was resuspended in $H_2O$ or TE. Ligation of the isolated fragment into the vector was performed using DNA ligase (Boehringer Mannheim Corporation, Indianapolis, Ind.), as recommended by the manufacturer. The ligation reaction was incubated at 16° C. overnight. Bacterial transformations were performed using E. coli XL1-Blue competent cells. Unless indicated otherwise, transformations and bacterial re-streaks were plated on LB agar (Lennox) plates supplemented with 100 ug/ml ampicillin. All bacterial incubations (plates and liquid cultures) were conducted overnight (16 hours) at 37° C.

Screening of transformants to identify desired clones was accomplished by restriction enzyme digestion of mini-prep DNA and/or by colony PCR. Mini-prep DNA was prepared according to Molecular Cloning: A Laboratory Manual, Example 1

Antigen Production

Preparation of Recombinant FMDV VP1 Antigen

A. Construction of FMDV VP1 Expression Vectors (i) Construction of Synthetic VP1 Gene VP1 protein FMDV Taiwan Type O 97 sequence was retrieved from NCBI GenBank database (genbank accession number: GI5921457) and oligonucleotides for synthesis of the gene were synthesized at ResGen (Huntsville, Ala.). In the synthetic oligonucleotides, the native FMDV codons were altered to conform to *E. coli* codon bias in an effort to increase expression levels of the recombinant protein in *E. coli*. (see, for example, M. Gouy and C. Gautier, Nucleic Acids Research 10:7055 (1982); H. Grosjean and W. Fiers, Gene 18:199 (1982); J. Watson et al. (eds.), Molecular Biology of the Gene, 4th Ed., Benjamin Kumming Publishing Co., pp. 440 (1987)). The recursive PCR method was used to assemble the oligonucleotides into a full VP1 gene. The gene construction strategy involved synthesis of a series of overlapping oligonucleotides with complementary ends. When annealed, the ends served as primers for the extension of the complementary strand. The fragments were then amplified by outside primers.

The oligonucleotide was designed to contain a BamHI restriction site for cloning into the expression vector pGEX-4T-1. The anti-sense oligonucleotide contains a translational termination codon (TAA) and an EcoRI restriction site. When outside primers TW97-1 (SEQ ID NO: 1) and TW97-16 (SEQ ID NO: 16) were used, a full-length VP1 (213 amino acids) gene was synthesized (FIG. 4).

Recursive PCR (100 ul volume) was set up as follows: Vent DNA polymerase (1U) and 1× buffer, along with 25 uM of each dNTP (dATP, dCTP, dGTP, and dTTP), 50 pmol each of oligonucleotides TW97-1 (SEQ ID NO: 1) and TW97-16 (SEQ ID NO: 16), and 0.25 pmol each of oligonucleotides TW97-2 through TW97-15 (SEQ ID NO: 2 through SEQ ID NO: 15, respectfully). The reaction was incubated at 95° C. for 5 minutes, and then amplified with 30 cycles of 95° C. for 15 seconds, 58° C. for 15 seconds and 72° C. for 60 seconds, followed by incubation at 72° C. for 5 minutes. The PCR-derived product was purified using Qiagen PCR spin column.

(ii) Cloning of the PCR Product.

Figure 5:
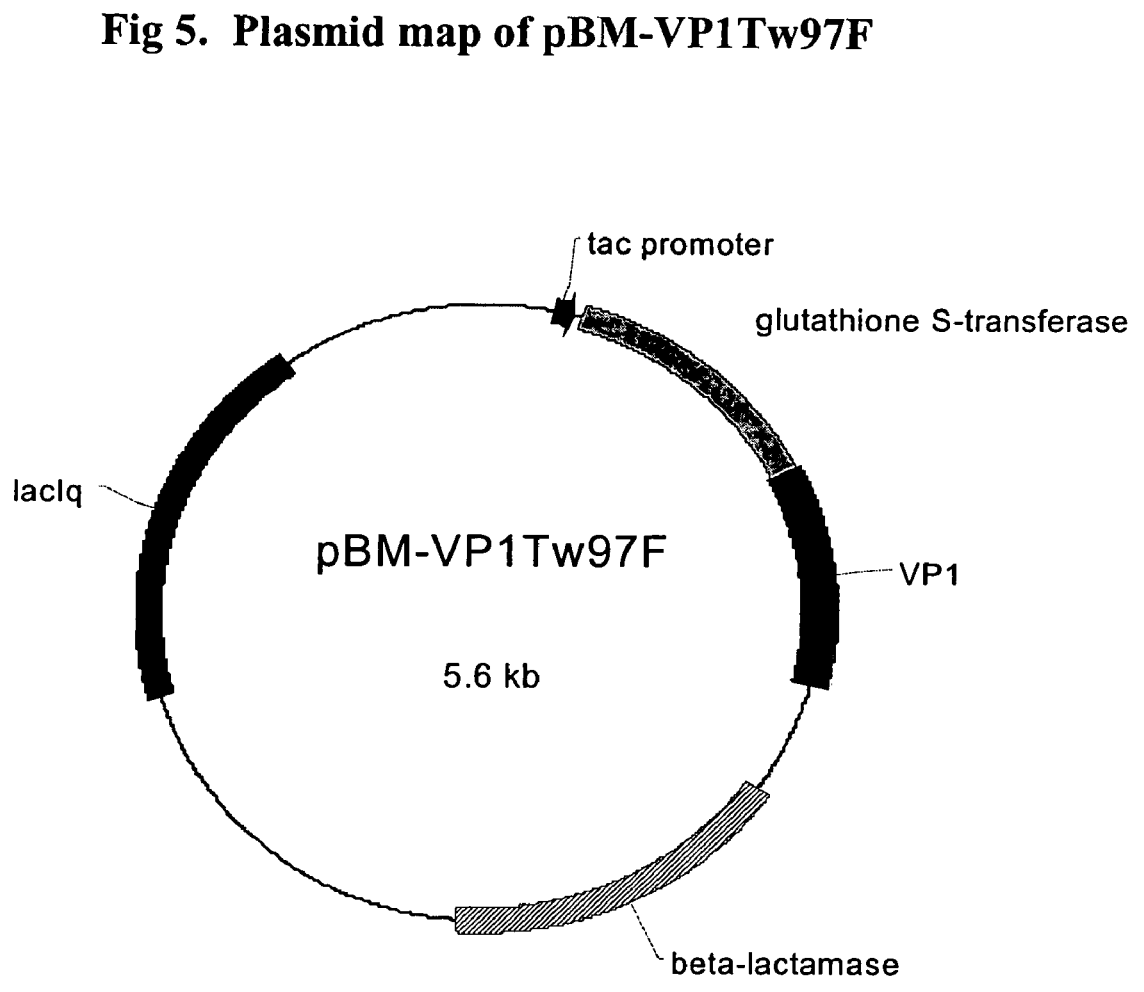

The PCR product amplified as described herein was digested with the restriction endonucleases Bam HI and Eco RI and ligated into the gel-purified vector pGEX-4T-1 that had been digested with Bam HI and Eco RI. The ligation product was used to transform XL-1 Blue competent cells. The transformed cells were plated on LB plates supplemented with 100 ug/ml ampicillin. Mini-prep DNAs were prepared from overnight cultures of colonies and digested with Bam HI and Eco RI to screen the desired clones. The clone with right insert was designated as pBM-VP1Tw97F (FIG. 5).

The pBM-VP1Tw97 clone was sequenced with the oligonucleotide primers pGEX5 (SEQ ID NO: 116) and pGEX3 (SEQ ID NO: 117).

B. Growth and Induction of *E. coli* Strains with VP1 Plasmids

Overnight seed cultures of each *E. coli* colonies were prepared in 500 ml sterile LB supplemented with 100 µg/ml ampicillin, and placed in a shaking orbital incubator at 37° C. unless otherwise indicated. Colonies containing desired clones were propagated from the transfer plate or stocked in glycerol at −70° C.

Fifty milliliter inoculums from seed cultures were transferred to flasks containing 0.5 liter sterile LB supplemented with 100 µg/ml ampicillin. Cultures were incubated at 37° C. until the cultures reached mid-logarithmic growth and then induced with 1 mM IPTG for 3 hours at 37° C. After the induction period, cells were pelleted by centrifugation and harvested following standard procedures currently used in the art. Pelleted cells were stored at −70° C. until further processed.

C. Preparation of VP1 Antigen

Frozen cells obtained above were resuspended in PBS with 1 mM PMSF. The cells were disrupted by ultrasonication (Branson). Inclusion bodies were separated from soluble proteins by centrifugation. These pelleted inclusion bodies were washed and pelleted sequentially in PBS followed by water. The washed inclusion bodies were resuspended in PBS and 5 M urea with a brief sonication. The inclusion bodies were then separated from the solubilized proteins by centrifugation. The pelleted inclusion bodies were fully solubilized in 7M guanidine-HCl. The solubilized recombinant antigens were clarified by centrifugation and passed through a 0.2 µm filter.

The guanidine-HCl solubilized fusion protein was denatured by diluting in water and precipitated by centrifugation. The pellet was washed with water and then resuspended in water. A 2M NaOH solution was added to solubilize the denatured protein completely and 2N HCl was added to neutralize the pH of the protein solution.

Example 2

Preparation of Recombinant FMDV 2C Antigen

A. Construction of FMDV 2C Expression Vector

The genome sequence of FMDV 2C protein was retrieved from NCBI GenBank database (GI: 5921457, O strain Chu-Pei) and oligonucleotides for the synthesis of the entire 2C gene were synthesized, and confirmed by sequencing, at ResGen (Huntsville, Ala.). The coding DNA sequence is 954 nucleotides long, which encodes 318 amino acids (FIG. 6).

(i) Construction Of Synthetic Full-Length 2C Gene

To obtain the 2C gene of FMDV, 24 oligonucleotide primers were synthesized, each with complementary ends, at Resgen. The recursive PCR method was used to assemble the oligonucleotides into a full-length 2C gene. The gene construction strategy involved synthesis of a series of overlapping oligonucleotides with complementary ends. When annealed, the ends served as primers for the extension of the complementary strand. The fragments were then amplified by excessive outside primers.

Due to the large size of the 2C gene that was to be synthesized, the oligonucleotides were divided into three groups and the respective recursive PCRs were performed. The three DNA products were designated as the A, B and C fragments. The B and C fragments were joined with PCR and then the B-C fragment was joined with A fragment to produce a full-length 2C gene. One of the oligonucleotides on the end of the full-length gene was designed to contain a BamHI restriction site for cloning into the expression vector pGEX-4T-1. The reaction was incubated at 95° C. for 5 minutes, and then amplified with 35 cycles of 95° C. for 30 seconds, 53° C. for 30 seconds and 73° C. for 100 seconds, followed by incubation at 73° C. for 5 minutes. An aliquot of the reaction mixture was analyzed by electrophoresis on agarose mini-gel.

(ii) Cloning of the PCR Product.

The amplified PCR product as described herein was digested with the restriction endonucleases Bam HI and Hind III and ligated into the vector pGEX-4T-1 that had been digested with Bam HI and Hind III. The ligation product was used to transform *E. coli* XL-1 Blue competent cells. The transformed cells were plated on LB plates supplemented with 100 ug/ml ampicillin. Mini-prep DNAs were prepared from overnight cultures of transformed colonies using QIAprep plasmid DNA mini-preparation kit and digested with Bam HI and Hind III to screen the desired clones. The clone with right insert was designated as pBM-2CTw97F (FIG. 7).

The pBM-2CTw97F clone was sequenced with the oligonucleotide primers pGEX5 (SEQ ID NO: 116), pGEX3 (SEQ ID NO: 117), 2C-25 (SEQ ID NO: 41) and 2C-26 (SEQ ID NO: 42).

B. Growth and Induction of *E. coli* Strains with FMDV 2C Plasmid

Overnight seed cultures of pGEX-2CTw97F were prepared in 500 ml sterile LB supplemented with 100 ug/ml ampicillin, and placed in a shaking orbital incubator at 37° C. A 50 ml inoculum from seed cultures was transferred to flask containing 0.5 liter sterile LB supplemented with 100 µg/ml ampicillin. Cultures were incubated at 37° C. until it reached mid-logarithmic growth and then induced with 1 mM IPTG for 3 hours at 37° C. After the induction period, cells were pelleted by centrifugation and harvested following standard procedures. The pelleted cells were stored at −70° C. until further process.

C. Preparation of FMDV2C Antigen

Frozen cells obtained above were resuspended in PBS with 1 mM PMSF and Triton X-100 detergent, and then disrupted by ultrasonication (Branson). Inclusion bodies were separated from soluble proteins by centrifugation. The protein fraction enriched with 2C was obtained through 3-4 rounds of washing off the contaminants and solubilization of the cell lysate pellet in urea or guanidin-HCl. Recombinant 2C was purified through size exclusion chromatography (FPLC, Sephacryl S 200 HR) under denaturing conditions (5N GuHCl, PBS (pH7.4)) and the eluted fraction containing 2C was identified by SDS-PAGE and then dialyzed against 20 mM phosphate buffer (pH 9.0). Sodium azide (0.05%) was added to the protein solution, which was stored at 4° C. For longer storage (over 1 month), the protein solution was aliquoted and frozen at −70° C.

Example 3

Preparation of Recombinant FMDV 3ABC Antigen

A. Construction of FMD V 3ABC Expression Vector

The genome sequence of FMDV 3ABC protein was retrieved from NCBI GenBank data (GI: 5921457, O strain Chu-Pei) and oligonucleotides for the synthesis of whole 3ABC gene and sequencing were synthesized at ResGen (Huntsville, Ala.). The coding DNA sequence is 1281 nucleotides long, which encodes 427 amino acids (FIG. 8).

(i) Construction of Synthetic Full-Length 3ABC Genes

To obtain the 3ABC gene of FMDV, 33 oligonucleotide primers were synthesized, each with complementary ends, at ResGen. The recursive PCR method was used to assemble the oligonucleotides into a full-length 3ABC gene. The gene construction strategy involved synthesis of a series of overlapping oligonucleotides with complementary ends. When annealed, the ends served as primers for the extension of the complementary strand. The fragments then were amplified using outside primers. Due to the large size of 3ABC gene to be synthesized, the oligonucleotides were divided into four groups and respective recursive PCRs were performed. The four DNAs were designated as the A, B, C or D fragment. The A and B fragments were joined and the C and D fragments were joined through PCR. Then the A-B fragment was joined with the C-D fragment to produce a full-length 3ABC gene.

One of the end oligonucleotides used in the recursive PCR above was designed to contain a BamHI restriction site for cloning into the expression vector pGEX-4T-1. The antisense oligonucleotide contains a translational termination codon (TAA) and an EcoRI restriction site. When N- and C-terminal primers, 3ABC-1 (SEQ ID NO: 43) and 3ABC-33 (SEQ ID NO: 75), were used, a full-length 3ABC (427 amino acids) gene was synthesized.

The PCR reaction (100 µl volume) was set up as follows: Vent DNA polymerase (1U) and 1× buffer, along with 25 µM of each dNTP (dATP, dCTP, dGTP, and dTTP), 4 µl 100 mM MgSO$_4$ and 100 pmol of each oligonucleotide. The template was mixture of the A-B fragment and the C-D fragment. The reaction was incubated at 95° C. for 5 minutes, and then amplified with 35 cycles of 95° C. for 30 seconds, 60° C. for 30 seconds and 73° C. for 120 seconds, followed by incubation at 73° C. for 5 minutes. The PCR-derived product was run on the agarose gel and the DNA band was excised and eluted from the gel using Quigen gel extraction kit.

(ii) Cloning of the PCR Product.

The PCR product amplified as described above was digested with the restriction endonucleases Bam HI and Hind III and ligated into the vector pGEX-4T-1 that had been digested with Bam HI and Hind III. The ligation product was used to transform *E. coli* XL-1 Blue competent cells. The transformed cells were plated on LB plates supplemented with 100 µg/ml ampicillin. Mini-prep DNAs were prepared from overnight cultures of transformed colonies using QIAprep plasmid DNA mini-preparation kit and digested with Bam HI and Hind III to screen for the desired clones. The clone with right insert was designated as pBM-3ABCTw97F (FIG. 9).

The pBM-3ABCTw97F clone was sequenced with the oligonucleotide primers pGEX5 (SEQ ID NO: 116), pGEX3 (SEQ ID NO: 117), 3ABC-36 (SEQ ID NO: 78) and 3ABC-37 (SEQ ID NO: 79).

B. Growth and Induction of *E. coli* Strains with 3ABC Plasmid

Overnight seed cultures of pGEX-3ABCTw97F were prepared in 500 ml sterile LB supplemented with 100 µg/ml ampicillin, and placed in a shaking orbital incubator at 37° C. A 50 ml inoculum from seed cultures was transferred to flask containing 0.5 liter sterile LB supplemented with 100 µg/ml ampicillin. Cultures were incubated at 37° C. until it reached mid-logarithmic growth and then induced with 1 mM IPTG for 3 hours at 37° C. After the induction period, cells were pelleted by centrifugation and harvested following standard procedures known in the art. Pelleted cells were stored at −70° C. until further process.

C. Preparation of FMDV 3ABC Antigen

Frozen cells obtained above were resuspended in PBS with 1 mM PMSF and Triton X-100 detergent and disrupted by ultrasonication (Branson). Inclusion bodies were separated from soluble proteins by centrifugation. Protein fraction enriched with 3ABC was obtained through 3-4 rounds of washing off the contaminants and solubilization of cell lysate pellet in urea. Recombinant 3ABC was run through ion-exchange chromatography (FPLC, Q-Sepharose FF) under denaturing condition (8M urea, 10 mM DTT, 20 mM potassium phosphate, pH 7.0) and eluted using a NaCl gradient. The eluted fraction was dialyzed against 20 mM phosphate buffer (pH 9.0). After measuring the protein concentration by the Bradford method and adding sodium azide to 0.05%, the protein solution was stored at 4° C. For longer storage (over 1 month), protein solution was aliquoted and frozen at −70° C.

Example 4

Preparation of Recombinant FMDV 3D Antigen

A. Construction of FMD V 3D Expression Vector (i) Construction of Synthetic Full-Length 3D Genes To obtain the 3D gene of FMDV, 36 oligonucleotides were syntheszied, each with complementary ends, at ResGen. We used the recursive PCR method to assemble the oligonucleotides into a full 3D gene (FIG. 10). The gene construction strategy involved synthesis of a series of overlapping oligonucleotides with complementary ends. When annealed, the ends served as primers for the extension of the complementary strand. The fragments were then amplified by excessive outside primers. Because of the large size of 3D gene to be synthesized, the oligonucleotides were divided into three groups and recursive PCRs were performed. The produced DNAs were designated as the A, B and C fragments. The B and C fragments were joined with PCR and then the B-C fragment was joined with the A fragment to produce the full-length 3D gene.

One of the end oligonucleotides was designed to contain a BamHI restriction site for cloning into the expression vector pGEX-4T-1. The anti-sense oligonucleotide contains a translational termination codon (TAA) and an EcoRI restriction site. When N- and C-terminal primers, 3d-1A (SEQ ID NO: 80) and 3d-36A (SEQ ID NO: 115), were used, a full-length 3D (470 amino acids) gene was synthesized. These steps are detailed herein below.

1. 3DA Fragment PCR

The PCR reaction (100 µl volume) was set up as follows: Vent DNA polymerase (1U) and 1× buffer, along with 25 µM of each dNTP (dATP, dCTP, dGTP, and dTTP), 4 µl 100 mM MgSO$_4$, 100 pmol each of oligonucleotides 3d-1A (SEQ ID NO: 80) and 3d-14 (SEQ ID NO: 93). The template was a mixture of 0.83 pmole of each of the oligonucleotides 3d-1A to 3d-14. The reaction was incubated at 95° C. for 5 minutes, and then amplified with 35 cycles of 95° C. for 30 seconds, 53° C. for 30 seconds and 73° C. for 100 seconds, followed by incubation at 73° C. for 5 minutes. An aliquot of the reaction mixture was analyzed by electrophoresis on agarose mini-gel.

2. 3 DB Fragment PCR

The PCR reaction (100 µl volume) was set up as follows: Vent DNA polymerase (1U) and 1× buffer, along with 25 µM of each dNTP (dATP, dCTP, dGTP, and dTTP), 4 µl 100 mM MgSO$_4$, 100 pmol each of oligonucleotides 3d-13 (SEQ ID NO: 92) and 3d-24 (SEQ ID NO: 103). The template was mixture of 0.83 pmole of each oligonucleotides 3d-13 to 3d-24. The reaction was incubated at 95° C. for 5 minutes, and then amplified with 35 cycles of 95° C. for 30 seconds, 55° C. for 30 seconds and 72° C. for 90 seconds, followed by incubation at 72° C. for 5 minutes. An aliquot of the reaction mixture was analyzed by electrophoresis on agarose mini-gel.

3. 3DC Fragment PCR

The PCR reaction (100 µl volume) was set up as follows: Vent DNA polymerase (1U) and 1× buffer, along with 25 µM of each dNTP (dATP, dCTP, dGTP, and dTTP), 4 µl 100 mM MgSO$_4$, 100 pmol each of oligonucleotides 3d-25 (SEQ ID NO: 104) and 3d-36A (SEQ ID NO: 115). The template was mixture of 0.83 pmole of each oligonucleotides 3d-25 to 3d-36A. The reaction was incubated at 95° C. for 5 minutes, and then amplified with 35 cycles of 95° C. for 30 seconds, 53° C. for 30 seconds and 73° C. for 100 seconds, followed by incubation at 73° C. for 5 minutes. An aliquot of the reaction mixture was analyzed by electrophoresis on agarose mini-gel.

4. 3 DB-C Fragment PCR

The PCR reaction (100 ul volume) was set up as follows: Vent DNA polymerase (1U) and 1× buffer, along with 25 µM of each dNTP (dATP, dCTP, dGTP, and dTTP), 4 µl 100 mM MgSO$_4$, 100 pmol each of oligonucleotides 3d-13 (SEQ ID NO: 92) and 3d-36A (SEQ ID NO: 115). The template was a mixture of the B and C fragments described above. The reaction was incubated at 95° C. for 5 minutes, and then amplified with 35 cycles of 95° C. for 30 seconds, 55° C. for 30 seconds and 73° C. for 90 seconds, followed by incubation at 73° C. for 5 minutes. An aliquot of the reaction mixture was analyzed by electrophoresis on agarose mini-gel.

5. Full-Length 3D (ABC) PCR

The PCR reaction (100 µl volume) was set up as follows: Vent DNA polymerase (1U) and 1× buffer, along with 25 µM of each dNTP (dATP, dCTP, dGTP, and dTTP), 4 µl 100 mM MgSO$_4$, 100 pmol each of oligonucleotides 3d-1A (SEQ ID NO: 80) and 3d-36A (SEQ ID NO: 115). The template was a mixture of A, B and C fragments. The reaction was incubated at 95° C. for 5 minutes, and then amplified with 35 cycles of 95° C. for 30 seconds, 60° C. for 30 seconds and 73° C. for 120 seconds, followed by incubation at 73° C. for 5 minutes. The PCR-derived product was run on the agarose gel and the DNA band was cut from the gel and then eluted using Quigen gel extraction kit.

(ii) Cloning of the PCR Product.

The PCR product amplified as described herein was digested with the restriction endonucleases Bam HI and Eco RI and ligated into the gel purified vector pGEX-4T-1 that had been digested with Bam HI and Eco RI. The ligation product was used to transform XL-1 Blue competent cells. The transformed cells were plated on LB plates supplemented with 100 µg/ml ampicillin. Mini-prep DNAs were prepared from overnight cultures of colonies and digested with Bam HI and Eco RI to screen the desired clones. The clone with right insert was designated as pBM-3DTw97F (FIG. 11).

B. Growth and Induction of E. coli Strains with pBM-3DTw97F

To express recombinant GST-3D protein, the pBM-3DTw97F plasmid was transformed into E. coli BL21 (DE3) and transformants were plated on LB-agar plate supplemented with 100 µg/ml ampicillin. Overnight seed cultures of the pBM-3DTw97F clone were prepared in 500 ml sterile LB supplemented with 100 µg/ml ampicillin, and placed in a shaking orbital incubator at 37° C. Fifty milliliter inoculums from seed cultures were transferred to flasks containing 0.5 liter sterile LB supplemented with 100 µg/ml ampicillin. Cultures were incubated at 37° C. until the cultures reached mid-logarithmic growth and then induced with 1 mM IPTG for 3 hours at 37° C. After the induction period, cells were pelleted by centrifugation and harvested following standard procedures. Pelleted cells were stored at −70° C. until further processed.

C. Preparation of GST-3D Protein

Frozen cells obtained above were resuspended in PBS with 1 mM PMSF. The cells were lysed by sonication (Branson, model S-125). A soluble crude lysate was prepared by centrifugation of the cell-lysate (10,000 rpm, 30 min) and filtered with 0.45 µm syringe filter (Sartorius). Glutathione affinity chromatography was carried out to purify rGST-3D protein. The soluble cell lysate was loaded onto glutathione sepharose 4B (Pharmacia) column equilibrated with PBS. After washing the column with three bed volumes of PBS, GST-3D was eluted with 10 mM reduced glutathione, 50 mM Tris-HCl, pH 8.0 buffer solution. The eluted fractions were analyzed on the 8% SDS-PAGE. The fractions that contained the fusion protein were dialyzed in PBS overnight.

Example 5

FMDV Antibody Detection Kit Formulation

A. Preparation of Antigen Printed Membrane

From the stock solution, recombinant 2C and 3ABC were mixed to 0.5 mg/ml each with 20 mM phosphate buffer (pH 9.0) and filtered through 0.22 μm filter unit Millex-GV (Millipore). An avidin solution (0.5 mg/ml) in PBS (pH 7.4) was used as an internal control. The antigen mixture and control solution were applied to the nitrocellulose membrane (S&S, 8 μm in pore size or equivalent) using Bio-Dot equipment (Bio-Dot) and following the manufacturers protocol. After the sample was dried in a low humidity room overnight, the membrane was blocked with 3% BSA in PBS for 20 min and then dried on a fan at least for 2 hours. The processed membrane plates are stored in an enclosed container with desiccant or low humidity room.

B. Preparation of Protein G and/or Protein A-Gold Conjugate

Recombinant protein G and/or protein A that had been engineered to eliminate any non-specific binding to serum albumin was purchased from Sigma and reconstituted with 10 mM sodium carbonate buffer (pH 9.6) to a concentration of 1 mg/ml. A gold particle suspension was adjusted to pH 9.0 with 50 mM potassium carbonate (pH 9.6) and the protein G and/or protein A was then added dropwise to the gold solution while stirring. The protein G and/or protein A was added so that a final concentration of 10 μg/ml was obtained. The solution was further stirred for 15 min. Next, 30 μl of 15% BSA solution was added per ml of gold particle suspension. After stirring for another 15 min, coupled gold solution was centrifuged and the supernatant was discarded, thereby removing any unbound protein G and/or protein A. To the pellet of 200 ml of coupled gold solution, 12 ml of 2% BSA (in deionized water) was added. The pellet solution was then sonicated in a sonic bath (Branson model #2200 or equivalent) to resuspend the pellet. The suspension was centrifuged again and the final pellet was suspended in the same volume of 2% BSA (10 mM Sodium carbonate, pH 9.6) and stored in refrigerator.

C. Preparation of Biotin-BSA-Gold Conjugate: Control Indicator

Biotinylated BSA (Pierce) was purchased and was coupled to the gold. The conjugation procedures were basically the same as described as for protein G and/or protein A above. Ten micrograms of biotinylated BSA per ml of gold particle suspension was added to the gold solution, which had been adjusted to pH 4.4 by adding 40 mM phosphoric acid with vigorous stirring. After about 1 min, 16.6 μl of 40 mM potassium carbonate per ml of coupled gold solution was added and allowed to stir for 10-15 min. At the end of the coupling reaction, 30 μl of 15% BSA solution was added per ml of gold particle suspension. After stirring for another 15 min, the Biotin-BSA coupled gold conjugate suspension was centrifuged and the supernatant was discarded to remove any unbound Biotin-BSA. The pellet from 200 ml of coupled gold solution was washed with 12 ml of 2% BSA (10 mM Sodium phosphate, pH 7.5). The resultant pellet was then resuspended in the same volume of 2% BSA (10 mM Sodium phosphate, pH 7.5) and stored in refrigerator.

D. Preparation of the Dye-Pad

Protein G and/or protein A coupled gold solution was diluted using dye dilution buffer (1% casein, 100 mM sodium phosphate, pH 7.0). Biotin-BSA coupled gold solution was added to generate the control line, which binds to avidin on the membrane (see FIG. 3). A lysate of the same *E. coli* strain used for production of recombinant FMDV antigens, but without a recombinant plasmid, was added to eliminate any anti-*E. coli* antibodies that might be present in the sample. The diluted gold solution was spread onto the Lydall pad strip (microglass paper) and dried in a lyophilizer. The Lydall pad was pre-soaked in pretreatment buffer (1% NP-40, 20 mM EDTA, 0.25% L-7600, 1% PVP 10, 10 mM sodium phosphate and 0.1% sodium azide, pH 7.0), excess liquid was blotted off, and the pad was dried on a fan. The pad is stored in a low humidity room until use.

E. Filter Pad Preparation

The cellulose filter paper was pre-soaked in pretreatment buffer (0.5% NP-40, 2% β-lactose, 1% PEG 15K, 100 mM sodium phosphate, and 0.1% sodium azide, pH 7.0) excess liquid was blotted off, and the paper was dried on a fan. The prepared filter pad was stored in a low humidity room.

F. Device Assembly

A protective sheet at the top of the plate was peeled off and the absorbent pad was attached along the long axis of the plate. A protective sheet at the bottom of the plate was peeled off and the dye pad was attached beneath the test membrane area along the long axis of the plate. The dye pad should overlap the bottom of the test membrane about 2-3 mm. Next, the filter pad was attached to the plate to cover the bottom of the dye pad. Finally, the dressed membrane plate was cut into 0.765 cm wide strips (FIG. 2).

Example 6

Kit Assay

A schematic diagram of the test kit is shown in FIG. 12. A test sample containing antibodies to FMDV or infected with FMDV (membrane shown on the left) will display a positive signal when contacted with FMDV antigen or FMDV antibodies, respectively. This is indicated by the color reaction at the band containing the immobilized capture reagent (FMDV antigen or FMDV antibodies; T), whereas a sample that does not contain FMDV (membrane shown on the right) will not display any color at the test band (T). A positive control is incorporated into the test kit by applying an albumin-biotin gold conjugate to the filter pad containing the labeled reagent. The albumin-biotin gold conjugate will bind to the avidin in the control band, thus the control band will be positive in both the test strips.

FIG. 13 is a schematic diagram of a two-line test kit configuration. An animal infected with FMDV, as shown in the figure labeled "infected", will reveal a positive signal on both the T1 (which contains SPs VP1 or 3D) and T2 (which contains NSPs 2C or 3ABC) test bands. The vaccinated sample will only reveal a positive signal at the T1 test band. No antibodies to NSPs and no NSP antigens will be present in the vaccinated sample. Thus the present invention is able to differentiate, within a very short time period, between the infected animal and one that is immune to infection (i.e., has been vaccinated).

Results

Analysis of Whole Blood and Serum Samples in FMDV-Infected Animals

Both whole blood and serum samples from FMDV-infected sheep (3) and goats (3) were analyzed for the presence of antibodies to the non-structural proteins 2C and 3ABC (Tables 1 and 2).

TABLE 1

Results Of Pen-Side Test Using Whole Blood And Serum Samples From FMDV-Infected Sheep

| DPI | Ovine #716 | | Ovine #717 | | Ovine #718 | |
|---|---|---|---|---|---|---|
| | Whole blood | serum | Whole blood | serum | Whole blood | serum |
| 0 | − | − | − | − | − | − |
| 2 | − | − | − | − | − | − |
| 4 | − | − | − | − | − | − |
| 6 | − | − | − | − | − | − |
| 8 | + | ± | − | − | − | − |
| 10 | + | + | − | − | + | + |
| 12 | + | + | ± | ± | + | + |
| 14 | ++ | ++ | ++ | ++ | ++ | ++ |

Legend:
+++ Prominently Visible Line
++ Clearly Visible Line
+Detectable Line
±Unclear Line
−No Line

TABLE 2

Results Of Pen-Side Test Using Whole Blood And Serum Samples From FMDV-Infected Goats

| DPI | Caprine #804 | | Caprine #808 | | Caprine #809 | |
|---|---|---|---|---|---|---|
| | Whole blood | serum | Whole blood | serum | Whole blood | serum |
| 0 | − | − | − | − | − | − |
| 2 | − | − | − | − | − | − |
| 4 | − | − | − | − | − | − |
| 6 | − | − | − | − | − | − |
| 8 | + | + | − | − | − | − |
| 10 | + | + | + | + | ± | + |
| 12 | + | + | ++ | ++ | ++ | ++ |
| 14 | ++ | ++ | ++ | ++ | ++ | ++ |

Legend:
+++ Prominently Visible Line
++ Clearly Visible Line
+Detectable Line
±Unclear Line
−No Line A positive signal was first detected at 8 days post infection (DPI) in ovine #716. There was no difference in the results from a whole blood sample or a serum sample.

Antibodies in ovine #717 were also detected, although a positive signal was not detected until 12 DPI. The antibodies in the whole blood and serum samples were detected at the same time after infection.

Antibodies in ovine #718 were detected at 10 DPI. As in ovine #716 and #717, the antibodies in the whole blood and serum samples were detected on the same DPI after infection.

The time frame in which the antibodies to the non-structural proteins in FMDV were detected in the goats (Table 2) was similar to those described for the sheep (Table 1). The anti-non-structural protein antibodies in the three goats were detected in both the whole blood and serum between day 8 and day 10 post infection.

Performance Characteristics of the Assay

A total of 1540 identified clinical samples from cattle, swine, goat and sheep sera, provided by PIADC, were tested at the Plum Island Animal Disease Center, USDA (Greenport, N.Y.) using the assay of the invention and commercially available ELISA.

The samples were negative samples prior to vaccination, vaccinated samples that were not infected, and infected samples. The results, shown in Table 3 below, illustrate the excellent agreement between the assay of the invention and the reference ELISA.

The assay of the invention demonstrated a relative sensitivity of 98.6% (69/70) and relative specificity of 98.6% (1449/1470) when compared with the reference test. The overall accuracy was 98.6% (1518/1540). (see also Table 4)

TABLE 3

Rapid Immunoassay vs. ELISA Test Results

| | Rapid Immunoassay | | | ELISA (AHIS Plum Island) | | |
|---|---|---|---|---|---|---|
| | Positive | Negative | Total | Positive | Negative | Total |
| Infected (+) | 52 | 0 | 52 | 52 | 0 | 52 |
| Naïve (−) | 8 | 1003 | 1011 | 0 | 1011 | 1011 |
| Vaccinated | 1 | 109 | 110 | 0 | 110 | 110 |
| (−) single multi | 6 | 64 | 70 | 0 | 70 | 70 |
| Total | 67 | 1176 | 1243 | 52 | 1191 | 1243 |

Sensitivity and Specificity of the Test Device

The sensitivity and specificity of the assay device disclosed herein was determined on the basis of samples that had been previously tested using the standard test method (ELISA). Antibodies against the 3ABC protein (one of the non-structural proteins) were measured 10 DPI using the method disclosed herein. The results shown in Table 4 reveal that the assay method of the present invention provides a sensitive, accurate and specific assay system that distinguishes, simultaneously, between an infected animal and one that is protected from infection (i.e., vaccinated) in a single step within 30 minutes.

TABLE 4

The Sensitivity And Specificity Of The Pen-Side Test For Bovine, Swine, Ovine, And Caprine

| Relative (%) | Bovine | Swine | Ovine | Caprine |
|---|---|---|---|---|
| Sensitivity | 95.6 | 100 | 100 | 100 |
| | (22/23) | (12/12) | (13/13) | (8/8) |
| Specificity | 98.5 | 99.3 | 100 | 96.8 |
| | (316/320)) | (796/801) | (31/31) | (30/31) |

TABLE 4-continued

The Sensitivity And Specificity Of The Pen-Side
Test For Bovine, Swine, Ovine, And Caprine

| Relative (%) | Bovine | Swine | Ovine | Caprine |
|---|---|---|---|---|
| Accuracy | 98.8 (338/343) | 99.3 (808/813) | 100 (43/43) | 97.4 (38/39) |

Efficacy of the Assay Device

FIGS. 14-17 compare the efficacy of the standard ELISA test to that of the assay presented herein. Antibodies to 3ABC were detected 6-7 DPI in bovine #19 and 21 (FIGS. 14-15), whereas the standard ELISA remained negative until 9 DPI. FIGS. 16-17 show the efficacy of the assay in pigs. Antibodies were detected in swine #183 12 DPI, while seroconversion in swine #186 was detected 10 DPI. While efficacy of the ELISA method was similar, the results of this method are not available for a few days. The results of the assay of the invention are available within 30 minutes, a significant advantage since FMDV is highly contagious and will spread rapidly through a herd.

The foregoing descriptions of specific embodiments of the present invention have been presented for the purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A single step test device for simultaneously detecting and differentiating between a Foot-and-Mouth Disease Virus (FMDV) infection and FMDV vaccination in a test sample, comprising, a membrane strip, said membrane strip comprising an application point for a fluid test sample comprising a labeled binding partner and a labeled control reagent, wherein said fluid test sample moves from a proximal end to a distal end by capillary action, and wherein said distal end of said strip contains a zone having at least one immobilized capture reagent capable of selectively binding an antibody specific for an FMDV structural protein, said FMDV structural protein comprising at least one of VP1, VP2, VP3 or VP4, and a second zone having at least one immobilized capture reagent capable of selectively binding an antibody specific for an FMDV non-structural protein, said FMDV non-structural protein comprising at least one of 3D, 2C or 3ABC, and a third zone of immobilized control capture reagent, and wherein said labeled binding partner is capable of forming a complex with an analyte in said fluid test sample forming a specific binding complex and wherein said capture reagent capable of selectively binding the antibody specific for the FMDV structural protein and/or said capture reagent capable of selectively binding the antibody specific for the FMDV non-structural protein is capable of binding said specific binding complex, wherein the device distinguishes infection from vaccination in a bovine test sample between about 6 to 8 days post infection with at least a 98% accuracy.

2. The test device according to claim 1, wherein the membrane strip material comprises nitrocellulose, cellulose acetate, polyester, poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), porous polyethylene frit or pads, or glass fiber filter paper.

3. The test device according to claim 1, wherein the membrane strip reveals at least two positive signals detectable by eye and/or by table top reader at two separate zones for an analyte obtained from an infected subject.

4. The test device according to claim 1, wherein the membrane strip reveals one positive signal for an analyte obtained from a vaccinated subject.

5. The test device according to claim 1, further comprising a filter element disposed onto or adjacent the application point and proximally to the first zone, the second zone and the third zone, said filter element permitting passage of any specific immuno-complex in said sample, but impeding passage of larger components contained in said sample.

6. The device of claim 1, wherein the intensity of a signal obtained from a non-infected vaccinated subject positively coffelates with an efficacy of the vaccination of the non-infected vaccinated subject.

7. The device of claim 1, wherein the application point comprises a filter element permitting passage of any specific immuno-complex in said sample, but impeding passage of larger components contained in said sample.

8. The device of claim 1, wherein said labeled binding partner is at least one of VP1, 3D, 2C or 3ABC, protein A, and protein G.

9. The device of claim 8, wherein the labeled binding partner is capable of binding to antibodies to said structural protein or said nonstructural protein of FMDV.

10. The device of claim 8 wherein said labeling binding partner is labeled with colloidal gold sol or detectable fluorescent and/or chromogenic markers.

* * * * *

SEQUENCE LISTING

```
<160> NUMBER OF SEQ ID NOS: 117

<210> SEQ ID NO 1
<211> LENGTH: 63
<212> TYPE: DNA
<213> ORGANISM: Artificial Sequence
<220> FEATURE:
<223> OTHER INFORMATION: Synthetic oligonucleotide primer TW97-1

<400> SEQUENCE: 1
atccaaggat ccaccacctc tgcgggtgag tctgcggacc cggtgactgc caccgttgag      60
aac                                                                    63

<210> SEQ ID NO 2
<211> LENGTH: 61
<212> TYPE: DNA
<213> ORGANISM: Artificial Sequence
<220> FEATURE:
<223> OTHER INFORMATION: Synthetic oligonucleotide primer TW97-2

<400> SEQUENCE: 2
ccgtgtgctg gcgacgctga acttgggtct caccaccgta gttctcaacg gtggcagtca      60
c                                                                      61

<210> SEQ ID NO 3
<211> LENGTH: 60
<212> TYPE: DNA
<213> ORGANISM: Artificial Sequence
<220> FEATURE:
<223> OTHER INFORMATION: Synthetic oligonucleotide primer TW97-3

<400> SEQUENCE: 3
tcagcgtcgc cagcacacgg acagcgcgtt catcttggac cgtttcgtga aagttaagcc      60

<210> SEQ ID NO 4
<211> LENGTH: 62
<212> TYPE: DNA
<213> ORGANISM: Artificial Sequence
<220> FEATURE:
<223> OTHER INFORMATION: Synthetic oligonucleotide primer TW97-4

<400> SEQUENCE: 4
```

```
cagggatctg catcaggtcc aacacattaa cttgttcctt tggcttaact ttcacgaaac    60
gg                                                                  62

<210> SEQ ID NO 5
<211> LENGTH: 63
<212> TYPE: DNA
<213> ORGANISM: Artificial Sequence
<220> FEATURE:
<223> OTHER INFORMATION: Synthetic oligonucleotide primer TW97-5

<400> SEQUENCE: 5
tggacctgat gcagatccct gcccacacct tggtaggtgc gctcctgcgt acggccacct    60
act                                                                 63

<210> SEQ ID NO 6
<211> LENGTH: 60
<212> TYPE: DNA
<213> ORGANISM: Artificial Sequence
<220> FEATURE:
<223> OTHER INFORMATION: Synthetic oligonucleotide primer TW97-6

<400> SEQUENCE: 6
tcgccctcgt gcttaacggc cagctccagg tcagagaagt agtaggtggc cgtacgcagg    60

<210> SEQ ID NO 7
<211> LENGTH: 62
<212> TYPE: DNA
<213> ORGANISM: Artificial Sequence
<220> FEATURE:
<223> OTHER INFORMATION: Synthetic oligonucleotide primer TW97-7

<400> SEQUENCE: 7
gccgttaagc acgagggcga tctcacctgg gttccaaacg gcgcccctga gaccgcactg    60
ga                                                                  62

<210> SEQ ID NO 8
<211> LENGTH: 60
<212> TYPE: DNA
<213> ORGANISM: Artificial Sequence
<220> FEATURE:
<223> OTHER INFORMATION: Synthetic oligonucleotide primer TW97-8

<400> SEQUENCE: 8
gagcggttcc ttgtggtaag cggttgggtt ggtagtgttg tccagtgcgg tctcaggggc    60

<210> SEQ ID NO 9
<211> LENGTH: 64
<212> TYPE: DNA
<213> ORGANISM: Artificial Sequence
<220> FEATURE:
<223> OTHER INFORMATION: Synthetic oligonucleotide primer TW97-9

<400> SEQUENCE: 9
cttaccacaa ggaaccgctc acccgtctgg cgctgcctta cacggctcca caccgtgttt    60
tagc                                                                64

<210> SEQ ID NO 10
<211> LENGTH: 62
<212> TYPE: DNA
<213> ORGANISM: Artificial Sequence
<220> FEATURE:
<223> OTHER INFORMATION: Synthetic oligonucleotide primer TW97-10

<400> SEQUENCE: 10
```

```
tgctggtgtc accgtacttg ctgctaccgt tgtaaacggt cgctaaaaca cggtgtggag    60
cc                                                                  62

<210> SEQ ID NO 11
<211> LENGTH: 62
<212> TYPE: DNA
<213> ORGANISM: Artificial Sequence
<220> FEATURE:
<223> OTHER INFORMATION: Synthetic oligonucleotide primer TW97-11

<400> SEQUENCE: 11
caagtacggt gacaccagca ctaacaacgt gcgtggtgac ctgcaagtgt tagctcagaa    60
gg                                                                  62

<210> SEQ ID NO 12
<211> LENGTH: 65
<212> TYPE: DNA
<213> ORGANISM: Artificial Sequence
<220> FEATURE:
<223> OTHER INFORMATION: Synthetic oligonucleotide primer TW97-12

<400> SEQUENCE: 12
gatggcaccg aagttgaagg aggtaggcag agtacgttct gccttctgag ctaacacttg    60
caggt                                                               65

<210> SEQ ID NO 13
<211> LENGTH: 62
<212> TYPE: DNA
<213> ORGANISM: Artificial Sequence
<220> FEATURE:
<223> OTHER INFORMATION: Synthetic oligonucleotide primer TW97-13

<400> SEQUENCE: 13
tccttcaact tcggtgccat caaggcaact cgtgttactg aactgctcta ccgtatgaag    60
cg                                                                  62

<210> SEQ ID NO 14
<211> LENGTH: 60
<212> TYPE: DNA
<213> ORGANISM: Artificial Sequence
<220> FEATURE:
<223> OTHER INFORMATION: Synthetic oligonucleotide primer TW97-14

<400> SEQUENCE: 14
ttgaatggcg agcagcggac gcggacagta ggtctcggca cgcttcatac ggtagagcag    60

<210> SEQ ID NO 15
<211> LENGTH: 60
<212> TYPE: DNA
<213> ORGANISM: Artificial Sequence
<220> FEATURE:
<223> OTHER INFORMATION: Synthetic oligonucleotide primer TW97-15

<400> SEQUENCE: 15
gtccgctgct cgccattcaa ccgagcgacg ctcgtcacaa gcagcgtatt gtggcaccgg    60

<210> SEQ ID NO 16
<211> LENGTH: 50
<212> TYPE: DNA
<213> ORGANISM: Artificial Sequence
<220> FEATURE:
<223> OTHER INFORMATION: Synthetic oligonucleotide primer TW97-16
```

-continued

```
<400> SEQUENCE: 16
gcctatgaat tcttacagca gctgttttgc cggtgccaca atacgctgct            50

<210> SEQ ID NO 17
<211> LENGTH: 62
<212> TYPE: DNA
<213> ORGANISM: Artificial Sequence
<220> FEATURE:
<223> OTHER INFORMATION: Synthetic oligonucleotide primer 2C-1

<400> SEQUENCE: 17
gcaggatccg acgacgacga caaactcaaa gcacgtgaca tcaacgacat atttgccgtt  60
ct                                                                62

<210> SEQ ID NO 18
<211> LENGTH: 60
<212> TYPE: DNA
<213> ORGANISM: Artificial Sequence
<220> FEATURE:
<223> OTHER INFORMATION: Synthetic oligonucleotide primer 2C-2

<400> SEQUENCE: 18
ttgctgtata aacggcaaga attcttgcca ctcaccgacc agtttgacta ggaccggtag  60

<210> SEQ ID NO 19
<211> LENGTH: 60
<212> TYPE: DNA
<213> ORGANISM: Artificial Sequence
<220> FEATURE:
<223> OTHER INFORMATION: Synthetic oligonucleotide primer 2C-3

<400> SEQUENCE: 19
tcaaactgat cctggccatc cgcgactgga ttaaggcatg gatcgcctca gaagagaagt  60

<210> SEQ ID NO 20
<211> LENGTH: 60
<212> TYPE: DNA
<213> ORGANISM: Artificial Sequence
<220> FEATURE:
<223> OTHER INFORMATION: Synthetic oligonucleotide primer 2C-4

<400> SEQUENCE: 20
ctagcggagt cttctcttca acagtggta ctgtctggac cacggaccgt aggaactttc   60

<210> SEQ ID NO 21
<211> LENGTH: 60
<212> TYPE: DNA
<213> ORGANISM: Artificial Sequence
<220> FEATURE:
<223> OTHER INFORMATION: Synthetic oligonucleotide primer 2C-5

<400> SEQUENCE: 21
gtgcctggca tccttgaaag tcaacgggat ctcaatgacc ccggcaaata caaggaggcc  60

<210> SEQ ID NO 22
<211> LENGTH: 60
<212> TYPE: DNA
<213> ORGANISM: Artificial Sequence
<220> FEATURE:
<223> OTHER INFORMATION: Synthetic oligonucleotide primer 2C-6

<400> SEQUENCE: 22
ggccgtttat gttcctccgg ttccttaccg acctgttgcg cgcagttcgc acaaacttct  60
```

<210> SEQ ID NO 23
<211> LENGTH: 60
<212> TYPE: DNA
<213> ORGANISM: Artificial Sequence
<220> FEATURE:
<223> OTHER INFORMATION: Synthetic oligonucleotide primer 2C-7

<400> SEQUENCE: 23
gcgtcaagcg tgtttgaaga gcgggaacgt gcacattgcc aatctgtgta aagtggtcgc    60

<210> SEQ ID NO 24
<211> LENGTH: 60
<212> TYPE: DNA
<213> ORGANISM: Artificial Sequence
<220> FEATURE:
<223> OTHER INFORMATION: Synthetic oligonucleotide primer 2C-8

<400> SEQUENCE: 24
ttagacacat tcaccagcg aggccgcggg tcgttcagct ctgggcttgg tcaccagcac    60

<210> SEQ ID NO 25
<211> LENGTH: 60
<212> TYPE: DNA
<213> ORGANISM: Artificial Sequence
<220> FEATURE:
<223> OTHER INFORMATION: Synthetic oligonucleotide primer 2C-9

<400> SEQUENCE: 25
gacccgaacc agtggtcgtg tgccttcgcg gcaaatccgg cacaaggaaa agcatcctcg    60

<210> SEQ ID NO 26
<211> LENGTH: 60
<212> TYPE: DNA
<213> ORGANISM: Artificial Sequence
<220> FEATURE:
<223> OTHER INFORMATION: Synthetic oligonucleotide primer 2C-10

<400> SEQUENCE: 26
gtgttccttt tcgtaggagc gcttgcacga gcgcgtccgt taaaggtgtg tgaagtgacc    60

<210> SEQ ID NO 27
<211> LENGTH: 60
<212> TYPE: DNA
<213> ORGANISM: Artificial Sequence
<220> FEATURE:
<223> OTHER INFORMATION: Synthetic oligonucleotide primer 2C-11

<400> SEQUENCE: 27
atttccacac acttcactgg taggaccgac tcggtctggt actgcccgcc cgaccctgac    60

<210> SEQ ID NO 28
<211> LENGTH: 60
<212> TYPE: DNA
<213> ORGANISM: Artificial Sequence
<220> FEATURE:
<223> OTHER INFORMATION: Synthetic oligonucleotide primer 2C-12

<400> SEQUENCE: 28
tgacgggcgg gctgggactg gtgaaactgc caatgttagt cgtctggcag cagcactacc    60

<210> SEQ ID NO 29
<211> LENGTH: 60
<212> TYPE: DNA
<213> ORGANISM: Artificial Sequence
<220> FEATURE:
<223> OTHER INFORMATION: Synthetic oligonucleotide primer 2C-13

<400> SEQUENCE: 29
gcagaccgtc gtcgtgatgg acgacttggg ccaaaaccca gacggcaaag acttcaagta    60

<210> SEQ ID NO 30
<211> LENGTH: 60
<212> TYPE: DNA
<213> ORGANISM: Artificial Sequence
<220> FEATURE:
<223> OTHER INFORMATION: Synthetic oligonucleotide primer 2C-14

<400> SEQUENCE: 30
ctgccgtttc tgaagttcat gaaacgggtt taccagaggt ggtgcccaa gtagggcgga    60

<210> SEQ ID NO 31
<211> LENGTH: 60
<212> TYPE: DNA
<213> ORGANISM: Artificial Sequence
<220> FEATURE:
<223> OTHER INFORMATION: Synthetic oligonucleotide primer 2C-15

<400> SEQUENCE: 31
ccacggggtt catcccgcct atggcctcgc tcgaggataa gggtaaaccc ttcaacagca    60

<210> SEQ ID NO 32
<211> LENGTH: 60
<212> TYPE: DNA
<213> ORGANISM: Artificial Sequence
<220> FEATURE:
<223> OTHER INFORMATION: Synthetic oligonucleotide primer 2C-16

<400> SEQUENCE: 32
cccatttggg aagttgtcgt tccagtatta tcgatgttgg ttggacatga gccctaagtg    60

<210> SEQ ID NO 33
<211> LENGTH: 60
<212> TYPE: DNA
<213> ORGANISM: Artificial Sequence
<220> FEATURE:
<223> OTHER INFORMATION: Synthetic oligonucleotide primer 2C-17

<400> SEQUENCE: 33
aacctgtact cgggattcac cccaaagacc atggtgtgcc ccgatgcgct taaccggagg    60

<210> SEQ ID NO 34
<211> LENGTH: 60
<212> TYPE: DNA
<213> ORGANISM: Artificial Sequence
<220> FEATURE:
<223> OTHER INFORMATION: Synthetic oligonucleotide primer 2C-18

<400> SEQUENCE: 34
ggctacgcga attggcctcc aaagtgaaac tgtagctgca ctcgcggttt ctgcccatgt    60

<210> SEQ ID NO 35
<211> LENGTH: 60
<212> TYPE: DNA
<213> ORGANISM: Artificial Sequence
<220> FEATURE:
<223> OTHER INFORMATION: Synthetic oligonucleotide primer 2C-19

<400> SEQUENCE: 35
gagcgccaaa gacgggtaca agatcaacaa caaactggac atagtcaaag cacttgaaga    60

<210> SEQ ID NO 36
<211> LENGTH: 60

```
<212> TYPE: DNA
<213> ORGANISM: Artificial Sequence
<220> FEATURE:
<223> OTHER INFORMATION: Synthetic oligonucleotide primer 2C-20

<400> SEQUENCE: 36
tatcagtttc gtgaacttct gtgggtgcga ttgggccacc gctacaaggt tatgctgacg      60

<210> SEQ ID NO 37
<211> LENGTH: 60
<212> TYPE: DNA
<213> ORGANISM: Artificial Sequence
<220> FEATURE:
<223> OTHER INFORMATION: Synthetic oligonucleotide primer 2C-21

<400> SEQUENCE: 37
cgatgttcca atacgactgc gctcttctca acggaatggc cgttgaaatg aagagaatgc      60

<210> SEQ ID NO 38
<211> LENGTH: 60
<212> TYPE: DNA
<213> ORGANISM: Artificial Sequence
<220> FEATURE:
<223> OTHER INFORMATION: Synthetic oligonucleotide primer 2C-22

<400> SEQUENCE: 38
gcaactttac ttctcttacg tcgttctgta caagttcgga gttggtggga aggtcttgta      60

<210> SEQ ID NO 39
<211> LENGTH: 60
<212> TYPE: DNA
<213> ORGANISM: Artificial Sequence
<220> FEATURE:
<223> OTHER INFORMATION: Synthetic oligonucleotide primer 2C-23

<400> SEQUENCE: 39
caaccaccct tccagaacat ctaccagctc gttcaggagg tgattgagcg ggtggaacta      60

<210> SEQ ID NO 40
<211> LENGTH: 56
<212> TYPE: DNA
<213> ORGANISM: Artificial Sequence
<220> FEATURE:
<223> OTHER INFORMATION: Synthetic oligonucleotide primer 2C-24

<400> SEQUENCE: 40
actaactcgc ccaccttgat gtgcttttcc acagctcggt gggctataaa tttgtc         56

<210> SEQ ID NO 41
<211> LENGTH: 30
<212> TYPE: DNA
<213> ORGANISM: Artificial Sequence
<220> FEATURE:
<223> OTHER INFORMATION: Synthetic oligonucleotide primer 2C-25

<400> SEQUENCE: 41
gtcgagaccc gaaccagtgg tcgtgtgcct                                       30

<210> SEQ ID NO 42
<211> LENGTH: 30
<212> TYPE: DNA
<213> ORGANISM: Artificial Sequence
<220> FEATURE:
<223> OTHER INFORMATION: Synthetic oligonucleotide primer 2C-26

<400> SEQUENCE: 42
```
aggcacacga ccactggttc gggtctcgac                                30

<210> SEQ ID NO 43
<211> LENGTH: 58
<212> TYPE: DNA
<213> ORGANISM: Artificial Sequence
<220> FEATURE:
<223> OTHER INFORMATION: Synthetic oligonucleotide primer 3ABC-1

<400> SEQUENCE: 43
gcaggatccg acgacgacga caaaatttca atcccttccc agaagtccgt gttgtact    58

<210> SEQ ID NO 44
<211> LENGTH: 60
<212> TYPE: DNA
<213> ORGANISM: Artificial Sequence
<220> FEATURE:
<223> OTHER INFORMATION: Synthetic oligonucleotide primer 3ABC-2

<400> SEQUENCE: 44
ggtcttcagg cacaacatga aggagtaact cttcccagtc gtgcttcgtc gctagctcaa   60

<210> SEQ ID NO 45
<211> LENGTH: 60
<212> TYPE: DNA
<213> ORGANISM: Artificial Sequence
<220> FEATURE:
<223> OTHER INFORMATION: Synthetic oligonucleotide primer 3ABC-3

<400> SEQUENCE: 45
cacgaagcag cgatcgagtt cttcgagggg atggtccacg attccatcaa agaggaactc   60

<210> SEQ ID NO 46
<211> LENGTH: 60
<212> TYPE: DNA
<213> ORGANISM: Artificial Sequence
<220> FEATURE:
<223> OTHER INFORMATION: Synthetic oligonucleotide primer 3ABC-4

<400> SEQUENCE: 46
taaggtagtt tctccttgag gctggggagt aagtcgtctg gagcaagcat tttgcgcgga   60

<210> SEQ ID NO 47
<211> LENGTH: 60
<212> TYPE: DNA
<213> ORGANISM: Artificial Sequence
<220> FEATURE:
<223> OTHER INFORMATION: Synthetic oligonucleotide primer 3ABC-5

<400> SEQUENCE: 47
ctcgttcgta aaacgcgcct tcaagcgcct gaaagagaac tttgaagttg tagccctgtg   60

<210> SEQ ID NO 48
<211> LENGTH: 60
<212> TYPE: DNA
<213> ORGANISM: Artificial Sequence
<220> FEATURE:
<223> OTHER INFORMATION: Synthetic oligonucleotide primer 3ABC-6

<400> SEQUENCE: 48
aaacttcaac atcgggacac aaactgggag aaccgtttgt atcactaata cgaggcggtt   60

<210> SEQ ID NO 49
<211> LENGTH: 60
<212> TYPE: DNA
<213> ORGANISM: Artificial Sequence

```
<220> FEATURE:
<223> OTHER INFORMATION: Synthetic oligonucleotide primer 3ABC-7

<400> SEQUENCE: 49
tagtgattat gctccgccaa gcgcgcaaga ggtaccaatc ggtggatgac ccactggacg       60

<210> SEQ ID NO 50
<211> LENGTH: 60
<212> TYPE: DNA
<213> ORGANISM: Artificial Sequence
<220> FEATURE:
<223> OTHER INFORMATION: Synthetic oligonucleotide primer 3ABC-8

<400> SEQUENCE: 50
ccacctactg ggtgacctgc cgctgcatcg agaaccgctg cgcctttttct tgggagacct       60

<210> SEQ ID NO 51
<211> LENGTH: 60
<212> TYPE: DNA
<213> ORGANISM: Artificial Sequence
<220> FEATURE:
<223> OTHER INFORMATION: Synthetic oligonucleotide primer 3ABC-9

<400> SEQUENCE: 51
gcggaaaaga accctctgga gacgagtgcc gctagcgctg tcggtttcag agagagatcc       60

<210> SEQ ID NO 52
<211> LENGTH: 60
<212> TYPE: DNA
<213> ORGANISM: Artificial Sequence
<220> FEATURE:
<223> OTHER INFORMATION: Synthetic oligonucleotide primer 3ABC-10

<400> SEQUENCE: 52
agccaaagtc tctctctagg gggtggctcg ttccctgcgc gcttctgcgc ttgcgactcg       60

<210> SEQ ID NO 53
<211> LENGTH: 60
<212> TYPE: DNA
<213> ORGANISM: Artificial Sequence
<220> FEATURE:
<223> OTHER INFORMATION: Synthetic oligonucleotide primer 3ABC-11

<400> SEQUENCE: 53
cgaagacgcg aacgctgagc ccgtcgtgtt cggtagggaa caaccgcgag ctgaaggacc       60

<210> SEQ ID NO 54
<211> LENGTH: 60
<212> TYPE: DNA
<213> ORGANISM: Artificial Sequence
<220> FEATURE:
<223> OTHER INFORMATION: Synthetic oligonucleotide primer 3ABC-12

<400> SEQUENCE: 54
gttggcgctc atgcggccgg gttacctctc tgtctttggc gatttccact ttcgttttcg       60

<210> SEQ ID NO 55
<211> LENGTH: 60
<212> TYPE: DNA
<213> ORGANISM: Artificial Sequence
<220> FEATURE:
<223> OTHER INFORMATION: Synthetic oligonucleotide primer 3ABC-13

<400> SEQUENCE: 55
gtcagaaacc tcttaaagtg aaagccgagc tgccacaaca ggagggacca tacgccggcc       60
```

<210> SEQ ID NO 56
<211> LENGTH: 60
<212> TYPE: DNA
<213> ORGANISM: Artificial Sequence
<220> FEATURE:
<223> OTHER INFORMATION: Synthetic oligonucleotide primer 3ABC-14

<400> SEQUENCE: 56
gcttttgctt tcacctttag cggtttctgt ctctccattg ggccggcgta tggtccctcc      60

<210> SEQ ID NO 57
<211> LENGTH: 60
<212> TYPE: DNA
<213> ORGANISM: Artificial Sequence
<220> FEATURE:
<223> OTHER INFORMATION: Synthetic oligonucleotide primer 3ABC-15

<400> SEQUENCE: 57
ctaaaggtga aagcaaaagc ccccgtcgtg aaggaaggac cttacgaggg accggtgaag      60

<210> SEQ ID NO 58
<211> LENGTH: 60
<212> TYPE: DNA
<213> ORGANISM: Artificial Sequence
<220> FEATURE:
<223> OTHER INFORMATION: Synthetic oligonucleotide primer 3ABC-16

<400> SEQUENCE: 58
gaatgctccc tggccacttc tttggacagc gaaattttca ctttcgtttc ttgaactatc      60

<210> SEQ ID NO 59
<211> LENGTH: 60
<212> TYPE: DNA
<213> ORGANISM: Artificial Sequence
<220> FEATURE:
<223> OTHER INFORMATION: Synthetic oligonucleotide primer 3ABC-17

<400> SEQUENCE: 59
gaaagcaaag aacttgatag tcactgagag tggtgcgcca ccgaccgact tgcaaaagat      60

<210> SEQ ID NO 60
<211> LENGTH: 60
<212> TYPE: DNA
<213> ORGANISM: Artificial Sequence
<220> FEATURE:
<223> OTHER INFORMATION: Synthetic oligonucleotide primer 3ABC-18

<400> SEQUENCE: 60
ggctggctga acgttttcta ccagtacccg ttgtgattcg gtcagctcga gtaggagctg      60

<210> SEQ ID NO 61
<211> LENGTH: 60
<212> TYPE: DNA
<213> ORGANISM: Artificial Sequence
<220> FEATURE:
<223> OTHER INFORMATION: Synthetic oligonucleotide primer 3ABC-19

<400> SEQUENCE: 61
cagtcgagct catcctcgac ggcaagacgg tagccatttg ctgtgctacc ggagtgttcg      60

<210> SEQ ID NO 62
<211> LENGTH: 60
<212> TYPE: DNA
<213> ORGANISM: Artificial Sequence
<220> FEATURE:
<223> OTHER INFORMATION: Synthetic oligonucleotide primer 3ABC-20

<400> SEQUENCE: 62
gacacgatgg cctcacaagc cgtgacggat ggagcacgga gcagtagaga agcgcctttt    60

<210> SEQ ID NO 63
<211> LENGTH: 60
<212> TYPE: DNA
<213> ORGANISM: Artificial Sequence
<220> FEATURE:
<223> OTHER INFORMATION: Synthetic oligonucleotide primer 3ABC-21

<400> SEQUENCE: 63
cgtcatctct tcgcggaaaa gtacgacaag atcatgttgg acggcagagc cttgacagac    60

<210> SEQ ID NO 64
<211> LENGTH: 60
<212> TYPE: DNA
<213> ORGANISM: Artificial Sequence
<220> FEATURE:
<223> OTHER INFORMATION: Synthetic oligonucleotide primer 3ABC-22

<400> SEQUENCE: 64
tgccgtctcg gaactgtctg tcactgatgt ctcacaaact caaactctaa tttcattttc    60

<210> SEQ ID NO 65
<211> LENGTH: 60
<212> TYPE: DNA
<213> ORGANISM: Artificial Sequence
<220> FEATURE:
<223> OTHER INFORMATION: Synthetic oligonucleotide primer 3ABC-23

<400> SEQUENCE: 65
gtttgagatt aaagtaaaag gacaggacat gctctcagac gccgctctca tggtgttgca    60

<210> SEQ ID NO 66
<211> LENGTH: 60
<212> TYPE: DNA
<213> ORGANISM: Artificial Sequence
<220> FEATURE:
<223> OTHER INFORMATION: Synthetic oligonucleotide primer 3ABC-24

<400> SEQUENCE: 66
cggcgagagt accacaacgt ggcacccttac gcgcacgcac tgtagtgctt tgtgaaagca    60

<210> SEQ ID NO 67
<211> LENGTH: 60
<212> TYPE: DNA
<213> ORGANISM: Artificial Sequence
<220> FEATURE:
<223> OTHER INFORMATION: Synthetic oligonucleotide primer 3ABC-25

<400> SEQUENCE: 67
acatcacgaa acactttcgt gacgtagcga gaatgaagaa gggaaccccc gtcgtcggtg    60

<210> SEQ ID NO 68
<211> LENGTH: 60
<212> TYPE: DNA
<213> ORGANISM: Artificial Sequence
<220> FEATURE:
<223> OTHER INFORMATION: Synthetic oligonucleotide primer 3ABC-26

<400> SEQUENCE: 68
cccttggggg cagcagccac actagttgtt acgactgcag ccctctgagt ataagagacc    60

<210> SEQ ID NO 69

-continued

```
<211> LENGTH: 60
<212> TYPE: DNA
<213> ORGANISM: Artificial Sequence
<220> FEATURE:
<223> OTHER INFORMATION: Synthetic oligonucleotide primer 3ABC-27

<400> SEQUENCE: 69
gggagactca tattctctgg tgtagccctc acttacaagg acatcgtcgt gtgtatggat      60

<210> SEQ ID NO 70
<211> LENGTH: 60
<212> TYPE: DNA
<213> ORGANISM: Artificial Sequence
<220> FEATURE:
<223> OTHER INFORMATION: Synthetic oligonucleotide primer 3ABC-28

<400> SEQUENCE: 70
tgtagcagca cacataccta cctctgtggt acggacccga gaaacggatg tcccgtaggt      60

<210> SEQ ID NO 71
<211> LENGTH: 60
<212> TYPE: DNA
<213> ORGANISM: Artificial Sequence
<220> FEATURE:
<223> OTHER INFORMATION: Synthetic oligonucleotide primer 3ABC-29

<400> SEQUENCE: 71
ctttgcctac agggcatcca ccaaggcagg ctactgcgga ggagccgtcc tggcaaagga      60

<210> SEQ ID NO 72
<211> LENGTH: 60
<212> TYPE: DNA
<213> ORGANISM: Artificial Sequence
<220> FEATURE:
<223> OTHER INFORMATION: Synthetic oligonucleotide primer 3ABC-30

<400> SEQUENCE: 72
cctcggcagg accgtttcct gccccggctt tgcaagtagc aaccgtgggt gaggcgtcca      60

<210> SEQ ID NO 73
<211> LENGTH: 60
<212> TYPE: DNA
<213> ORGANISM: Artificial Sequence
<220> FEATURE:
<223> OTHER INFORMATION: Synthetic oligonucleotide primer 3ABC-31

<400> SEQUENCE: 73
ttggcaccca ctccgcaggt ggaaacggca taggatactg ttcgtgtgtt tcccgatcaa      60

<210> SEQ ID NO 74
<211> LENGTH: 60
<212> TYPE: DNA
<213> ORGANISM: Artificial Sequence
<220> FEATURE:
<223> OTHER INFORMATION: Synthetic oligonucleotide primer 3ABC-32

<400> SEQUENCE: 74
aagcacacaa agggctagtt acgaggactt ctacttccgt gtgtagctgg gacttggtgt      60

<210> SEQ ID NO 75
<211> LENGTH: 49
<212> TYPE: DNA
<213> ORGANISM: Artificial Sequence
<220> FEATURE:
<223> OTHER INFORMATION: Synthetic oligonucleotide primer 3ABC-33

<400> SEQUENCE: 75
```

```
tgcaagcttt tactcgtggt gtggttcagg gtcgatgtgt gccttcatc                49
```

<210> SEQ ID NO 76
<211> LENGTH: 35
<212> TYPE: DNA
<213> ORGANISM: Artificial Sequence
<220> FEATURE:
<223> OTHER INFORMATION: Synthetic oligonucleotide primer 3ABC-34

<400> SEQUENCE: 76

```
ctttaaaagt gaaagcaaag aacttgatag tcact                               35
```

<210> SEQ ID NO 77
<211> LENGTH: 35
<212> TYPE: DNA
<213> ORGANISM: Artificial Sequence
<220> FEATURE:
<223> OTHER INFORMATION: Synthetic oligonucleotide primer 3ABC-35

<400> SEQUENCE: 77

```
agtgactatc aagttctttg ctttcacttt taaag                               35
```

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide primer 3ABC-36

<400> SEQUENCE: 78

```
ccgtcgtgtt cggtagggaa                                                20
```

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide primer 3ABC-37

<400> SEQUENCE: 79

```
aaagtaaaag gacaggacat                                                20
```

<210> SEQ ID NO 80
<211> LENGTH: 42
<212> TYPE: DNA
<213> ORGANISM: Artificial Sequence
<220> FEATURE:
<223> OTHER INFORMATION: Synthetic oligonucleotide primer 3d-1A

<400> SEQUENCE: 80

```
gctatcggat ccgggttgat cgttgatacc agagatgtgg aa                       42
```

<210> SEQ ID NO 81
<211> LENGTH: 60
<212> TYPE: DNA
<213> ORGANISM: Artificial Sequence
<220> FEATURE:
<223> OTHER INFORMATION: Synthetic oligonucleotide primer 3d-2

<400> SEQUENCE: 81

```
tgggtgcaag cttggttttg cgcattacat ggacgcgctc ttccacatct ctggtatcaa    60
```

<210> SEQ ID NO 82
<211> LENGTH: 60
<212> TYPE: DNA

```
<213> ORGANISM: Artificial Sequence
<220> FEATURE:
<223> OTHER INFORMATION: Synthetic oligonucleotide primer 3d-3

<400> SEQUENCE: 82
caaaaccaag cttgcaccca ccgtcgcgca cggtgtgttc aatcctgagt tcgggcctgc    60

<210> SEQ ID NO 83
<211> LENGTH: 60
<212> TYPE: DNA
<213> ORGANISM: Artificial Sequence
<220> FEATURE:
<223> OTHER INFORMATION: Synthetic oligonucleotide primer 3d-4

<400> SEQUENCE: 83
aacaccttcg ttcagacgtg ggtccttgtt agacaaggcg gcaggcccga actcaggatt    60

<210> SEQ ID NO 84
<211> LENGTH: 60
<212> TYPE: DNA
<213> ORGANISM: Artificial Sequence
<220> FEATURE:
<223> OTHER INFORMATION: Synthetic oligonucleotide primer 3d-5

<400> SEQUENCE: 84
cacgtctgaa cgaaggtgtt gtcctcgatg aagtcatttt ctccaagcat aaaggagaca    60

<210> SEQ ID NO 85
<211> LENGTH: 60
<212> TYPE: DNA
<213> ORGANISM: Artificial Sequence
<220> FEATURE:
<223> OTHER INFORMATION: Synthetic oligonucleotide primer 3d-6

<400> SEQUENCE: 85
cagcggcgga acagcgcttt gtcctcctca gacatctttg tgtctccttt atgcttggag    60

<210> SEQ ID NO 86
<211> LENGTH: 60
<212> TYPE: DNA
<213> ORGANISM: Artificial Sequence
<220> FEATURE:
<223> OTHER INFORMATION: Synthetic oligonucleotide primer 3d-7

<400> SEQUENCE: 86
aaagcgctgt tccgccgctg cgctgctgac tacgcgtcac gcctgcacag tgtgctgggt    60

<210> SEQ ID NO 87
<211> LENGTH: 60
<212> TYPE: DNA
<213> ORGANISM: Artificial Sequence
<220> FEATURE:
<223> OTHER INFORMATION: Synthetic oligonucleotide primer 3d-8

<400> SEQUENCE: 87
ccttgattgc ctcgtaaatg ctcagtgggg catttgccgt acccagcaca ctgtgcaggc    60

<210> SEQ ID NO 88
<211> LENGTH: 60
<212> TYPE: DNA
<213> ORGANISM: Artificial Sequence
<220> FEATURE:
<223> OTHER INFORMATION: Synthetic oligonucleotide primer 3d-9

<400> SEQUENCE: 88
catttacgag gcaatcaagg gcgttgacgg actcgacgcc atggagccag acaccgcacc    60
```

```
<210> SEQ ID NO 89
<211> LENGTH: 60
<212> TYPE: DNA
<213> ORGANISM: Artificial Sequence
<220> FEATURE:
<223> OTHER INFORMATION: Synthetic oligonucleotide primer 3d-10

<400> SEQUENCE: 89
tgcaccgcgg cgtttcccct ggagggccca gggaaggcca ggtgcggtgt ctggctccat      60

<210> SEQ ID NO 90
<211> LENGTH: 60
<212> TYPE: DNA
<213> ORGANISM: Artificial Sequence
<220> FEATURE:
<223> OTHER INFORMATION: Synthetic oligonucleotide primer 3d-11

<400> SEQUENCE: 90
aggggaaacg ccgcggtgca cttatcgatt tcgagaacgg cacggtcgga cccgaggttg      60

<210> SEQ ID NO 91
<211> LENGTH: 60
<212> TYPE: DNA
<213> ORGANISM: Artificial Sequence
<220> FEATURE:
<223> OTHER INFORMATION: Synthetic oligonucleotide primer 3d-12

<400> SEQUENCE: 91
aacttgtatt ctcttttctc catgagcttc aaggcagcct caacctcggg tccgaccgtg      60

<210> SEQ ID NO 92
<211> LENGTH: 60
<212> TYPE: DNA
<213> ORGANISM: Artificial Sequence
<220> FEATURE:
<223> OTHER INFORMATION: Synthetic oligonucleotide primer 3d-13

<400> SEQUENCE: 92
gagaaaagag aatacaagtt tgtttgccag accttcctga aggacgaaat tcgcccgatg      60

<210> SEQ ID NO 93
<211> LENGTH: 60
<212> TYPE: DNA
<213> ORGANISM: Artificial Sequence
<220> FEATURE:
<223> OTHER INFORMATION: Synthetic oligonucleotide primer 3d-14

<400> SEQUENCE: 93
aaacgtcgac aatgcgagtc ttgccggcac gtactttctc catcgggcga atttcgtcct      60

<210> SEQ ID NO 94
<211> LENGTH: 60
<212> TYPE: DNA
<213> ORGANISM: Artificial Sequence
<220> FEATURE:
<223> OTHER INFORMATION: Synthetic oligonucleotide primer 3d-15

<400> SEQUENCE: 94
gactcgcatt gtcgacgttt tgcctgttga acacattctt tacaccagga tgatgattgg      60

<210> SEQ ID NO 95
<211> LENGTH: 60
<212> TYPE: DNA
<213> ORGANISM: Artificial Sequence
<220> FEATURE:
```

```
<223> OTHER INFORMATION: Synthetic oligonucleotide primer 3d-16

<400> SEQUENCE: 95
ctgcggcccg ttgtttgagt gcatttgtgc acaaaatctg ccaatcatca tcctggtgta    60

<210> SEQ ID NO 96
<211> LENGTH: 60
<212> TYPE: DNA
<213> ORGANISM: Artificial Sequence
<220> FEATURE:
<223> OTHER INFORMATION: Synthetic oligonucleotide primer 3d-17

<400> SEQUENCE: 96
actcaaacaa cgggccgcag attggctcag cggtcggttg caaccctgat gttgattggc    60

<210> SEQ ID NO 97
<211> LENGTH: 60
<212> TYPE: DNA
<213> ORGANISM: Artificial Sequence
<220> FEATURE:
<223> OTHER INFORMATION: Synthetic oligonucleotide primer 3d-18

<400> SEQUENCE: 97
cacacgtttc tgtattgggc gaagtgtgtg ccgaatctct gccaatcaac atcagggttg    60

<210> SEQ ID NO 98
<211> LENGTH: 60
<212> TYPE: DNA
<213> ORGANISM: Artificial Sequence
<220> FEATURE:
<223> OTHER INFORMATION: Synthetic oligonucleotide primer 3d-19

<400> SEQUENCE: 98
gcccaataca gaaacgtgtg ggacgtggac tattcggcct ttgatgcaaa ccactgcagc    60

<210> SEQ ID NO 99
<211> LENGTH: 60
<212> TYPE: DNA
<213> ORGANISM: Artificial Sequence
<220> FEATURE:
<223> OTHER INFORMATION: Synthetic oligonucleotide primer 3d-20

<400> SEQUENCE: 99
ccgtgcggaa cacctcttca acatgatgt tcatggcatc gctgcagtgg tttgcatcaa    60

<210> SEQ ID NO 100
<211> LENGTH: 60
<212> TYPE: DNA
<213> ORGANISM: Artificial Sequence
<220> FEATURE:
<223> OTHER INFORMATION: Synthetic oligonucleotide primer 3d-21

<400> SEQUENCE: 100
tgaagaggtg ttccgcacgg agttcggctt ccacccgaat gctgagtgga ttctgaagac    60

<210> SEQ ID NO 101
<211> LENGTH: 60
<212> TYPE: DNA
<213> ORGANISM: Artificial Sequence
<220> FEATURE:
<223> OTHER INFORMATION: Synthetic oligonucleotide primer 3d-22

<400> SEQUENCE: 101
gatgcgcttg ttctcatagg cgtgttccgt gttcacgaga gtcttcagaa tccactcagc    60
```

<210> SEQ ID NO 102
<211> LENGTH: 60
<212> TYPE: DNA
<213> ORGANISM: Artificial Sequence
<220> FEATURE:
<223> OTHER INFORMATION: Synthetic oligonucleotide primer 3d-23

<400> SEQUENCE: 102
cctatgagaa caagcgcatc actgttgaag gcgggatgcc atctggctgt tccgcaacaa      60

<210> SEQ ID NO 103
<211> LENGTH: 60
<212> TYPE: DNA
<213> ORGANISM: Artificial Sequence
<220> FEATURE:
<223> OTHER INFORMATION: Synthetic oligonucleotide primer 3d-24

<400> SEQUENCE: 103
tagagcacgt agatgttatt caaaattgtg ttgatgatgc ttgttgcgga acagccagat      60

<210> SEQ ID NO 104
<211> LENGTH: 60
<212> TYPE: DNA
<213> ORGANISM: Artificial Sequence
<220> FEATURE:
<223> OTHER INFORMATION: Synthetic oligonucleotide primer 3d-25

<400> SEQUENCE: 104
aataacatct acgtgctcta cgccttgcgt agacactatg aggggttga gctggacacc      60

<210> SEQ ID NO 105
<211> LENGTH: 60
<212> TYPE: DNA
<213> ORGANISM: Artificial Sequence
<220> FEATURE:
<223> OTHER INFORMATION: Synthetic oligonucleotide primer 3d-26

<400> SEQUENCE: 105
ttgccaccac gatgtcgtct ccataggaga tcatggtgta ggtgtccagc tcaaccccct      60

<210> SEQ ID NO 106
<211> LENGTH: 60
<212> TYPE: DNA
<213> ORGANISM: Artificial Sequence
<220> FEATURE:
<223> OTHER INFORMATION: Synthetic oligonucleotide primer 3d-27

<400> SEQUENCE: 106
agacgacatc gtggtggcaa gcgattatga tctggacttt gaggccctca agcctcactt      60

<210> SEQ ID NO 107
<211> LENGTH: 60
<212> TYPE: DNA
<213> ORGANISM: Artificial Sequence
<220> FEATURE:
<223> OTHER INFORMATION: Synthetic oligonucleotide primer 3d-28

<400> SEQUENCE: 107
gcttttgtca gctggagtaa tggtttggcc aagagatttg aagtgaggct tgagggcctc      60

<210> SEQ ID NO 108
<211> LENGTH: 60
<212> TYPE: DNA
<213> ORGANISM: Artificial Sequence
<220> FEATURE:
<223> OTHER INFORMATION: Synthetic oligonucleotide primer 3d-29

```
<400> SEQUENCE: 108
ttactccagc tgacaaaagc gacaaaggtt ttgttcttgg tcactccatt actgacgtca        60

<210> SEQ ID NO 109
<211> LENGTH: 60
<212> TYPE: DNA
<213> ORGANISM: Artificial Sequence
<220> FEATURE:
<223> OTHER INFORMATION: Synthetic oligonucleotide primer 3d-30

<400> SEQUENCE: 109
ccagtgccat aatccatgtg gaagtgtctt ttgaggaaag tgacgtcagt aatggagtga       60

<210> SEQ ID NO 110
<211> LENGTH: 60
<212> TYPE: DNA
<213> ORGANISM: Artificial Sequence
<220> FEATURE:
<223> OTHER INFORMATION: Synthetic oligonucleotide primer 3d-31

<400> SEQUENCE: 110
cacatggatt atggcactgg gttttacaaa cctgtgatgg cctcgaagac cctcgaggct       60

<210> SEQ ID NO 111
<211> LENGTH: 60
<212> TYPE: DNA
<213> ORGANISM: Artificial Sequence
<220> FEATURE:
<223> OTHER INFORMATION: Synthetic oligonucleotide primer 3d-32

<400> SEQUENCE: 111
acttctcctg gatggtccca cggcgtgcaa aggagaggat agcctcgagg gtcttcgagg       60

<210> SEQ ID NO 112
<211> LENGTH: 60
<212> TYPE: DNA
<213> ORGANISM: Artificial Sequence
<220> FEATURE:
<223> OTHER INFORMATION: Synthetic oligonucleotide primer 3d-33

<400> SEQUENCE: 112
tgggaccatc caggagaagt tgatttccgt ggcaggactc gccgtccact ccggaccaga       60

<210> SEQ ID NO 113
<211> LENGTH: 60
<212> TYPE: DNA
<213> ORGANISM: Artificial Sequence
<220> FEATURE:
<223> OTHER INFORMATION: Synthetic oligonucleotide primer 3d-34

<400> SEQUENCE: 113
aaagaggccc tggaagggct caaagagacg ccggtactcg tctggtccgg agtggacggc       60

<210> SEQ ID NO 114
<211> LENGTH: 60
<212> TYPE: DNA
<213> ORGANISM: Artificial Sequence
<220> FEATURE:
<223> OTHER INFORMATION: Synthetic oligonucleotide primer 3d-35

<400> SEQUENCE: 114
agcccttcca gggcctcttt gagattccaa gctacagatc actttacctg cgttgggtga      60

<210> SEQ ID NO 115
<211> LENGTH: 55
```

```
<212> TYPE: DNA
<213> ORGANISM: Artificial Sequence
<220> FEATURE:
<223> OTHER INFORMATION: Synthetic oligonucleotide primer 3d-36A

<400> SEQUENCE: 115
gcaatcgaat tcttatgcgt cgccgcacac ggcgttcacc caacgcaggt aaagt        55

<210> SEQ ID NO 116
<211> LENGTH: 20
<212> TYPE: DNA
<213> ORGANISM: Artificial Sequence
<220> FEATURE:
<223> OTHER INFORMATION: Synthetic oligonucleotide primer pGEX5

<400> SEQUENCE: 116
ctggcaagcc acgtttggtg                                              20

<210> SEQ ID NO 117
<211> LENGTH: 20
<212> TYPE: DNA
<213> ORGANISM: Artificial Sequence
<220> FEATURE:
<223> OTHER INFORMATION: Synthetic oligonucleotide primer pGEX3

<400> SEQUENCE: 117
ggagctgcat gtgtcagagg                                              20
```